(12) United States Patent
Hulvershorn et al.

(10) Patent No.: US 8,538,537 B2
(45) Date of Patent: Sep. 17, 2013

(54) SYSTEMS AND METHODS FOR PROVIDING TARGETED NEURAL STIMULATION THERAPY TO ADDRESS NEUROLOGICAL DISORDERS, INCLUDING NEUROPYSCHIATRIC AND NEUROPYSCHOLOGICAL DISORDERS

(75) Inventors: Justin Hulvershorn, Seattle, WA (US); Brad Fowler, Duvall, WA (US); Bradford Evan Gliner, Sammamish, WA (US); Leif R. Sloan, Seattle, WA (US); Brian Kopell, Milwaukee, WI (US); David Alan Soltysik, Seattle, WA (US)

(73) Assignee: Advanced Neuromodulations Systems, Inc., Plano, TX (US)

( * ) Notice: Subject to any disclaimer, the term of this patent is extended or adjusted under 35 U.S.C. 154(b) by 1315 days.

(21) Appl. No.: 12/330,437

(22) Filed: Dec. 8, 2008

(65) Prior Publication Data

US 2009/0149898 A1 Jun. 11, 2009

Related U.S. Application Data

(60) Provisional application No. 61/012,389, filed on Dec. 7, 2007, provisional application No. 61/086,203, filed on Aug. 5, 2008, provisional application No. 61/091,324, filed on Aug. 22, 2008, provisional application No. 61/105,747, filed on Oct. 15, 2008.

(51) Int. Cl.
*A61N 1/00* (2006.01)

(52) U.S. Cl.
USPC .......................................................... 607/45

(58) Field of Classification Search
USPC .................................................. 607/2, 3, 45
See application file for complete search history.

(56) References Cited

U.S. PATENT DOCUMENTS

| 3,653,385 A | 4/1972 | Burton |
| 3,731,681 A | 5/1973 | Blackshear et al. |

(Continued)

FOREIGN PATENT DOCUMENTS

| EP | 1048317 | 11/2000 |
| WO | WO 0197906 | 12/2001 |

(Continued)

OTHER PUBLICATIONS

Kennedy et al., "Changes in regional barin glucose metabolism measured with positron emission tomography after paroxetine treatment of major depression," Am. J. Psychiatry, 158(6): 899-905, 2001.

(Continued)

*Primary Examiner* — Christopher D Koharski
*Assistant Examiner* — Nadia Ahmad

(57) ABSTRACT

Systems and methods for providing targeted neural stimulation therapy to address neurological disorders, including neuropsychiatric and neuropsychological disorders are disclosed. A method for treating a patient's neurological disorder in accordance with a particular embodiment includes, in a patient identified as having at least one of a neuropsychological disorder and a neuropsychiatric disorder, implanting at least one stimulation electrode within the patient's skull cavity, and outside a cortical surface of the patient's brain. The electrode is implanted at a location in a range of about 15 mm to about 35 mm anterior to a precentral sulcus reference point that is positioned at the precentral sulcus and at the patient's middle frontal gyrus. The method can further include treating the patient's disorder by applying electrical stimulation to the patient via the at least one stimulation electrode.

18 Claims, 19 Drawing Sheets

(56) References Cited

U.S. PATENT DOCUMENTS

| | | |
|---|---|---|
| 3,951,147 A | 4/1976 | Tucker et al. |
| 4,692,147 A | 9/1987 | Duggan |
| 4,772,263 A | 9/1988 | Dorman et al. |
| 4,883,057 A | 11/1989 | Broderick |
| 4,892,538 A | 1/1990 | Aebischer et al. |
| 5,119,832 A | 6/1992 | Xavier |
| 5,125,888 A | 6/1992 | Howard et al. |
| 5,263,480 A | 11/1993 | Wernicke et al. |
| 5,299,569 A | 4/1994 | Wernicke et al. |
| 5,342,410 A | 8/1994 | Braverman |
| 5,423,877 A | 6/1995 | Mackey |
| 5,458,631 A | 10/1995 | Xavier |
| 5,470,846 A | 11/1995 | Sandyk et al. |
| 5,540,734 A | 7/1996 | Zabara |
| 5,585,118 A | 12/1996 | Stoll |
| 5,601,835 A | 2/1997 | Sabel et al. |
| 5,611,350 A | 3/1997 | John |
| 5,683,422 A | 11/1997 | Rise |
| 5,707,335 A | 1/1998 | Howard et al. |
| 5,711,316 A | 1/1998 | Elsberry et al. |
| 5,713,923 A | 2/1998 | Ward et al. |
| 5,716,377 A | 2/1998 | Rise et al. |
| 5,735,814 A | 4/1998 | Elsberry et al. |
| 5,750,103 A | 5/1998 | Cherksey |
| 5,752,911 A | 5/1998 | Canedo et al. |
| 5,779,694 A | 7/1998 | Howard et al. |
| 5,792,186 A | 8/1998 | Rise |
| 5,814,014 A | 9/1998 | Elsberry et al. |
| 5,832,932 A | 11/1998 | Elsberry et al. |
| 5,833,709 A | 11/1998 | Rise et al. |
| 5,840,069 A | 11/1998 | Robinson |
| 5,853,385 A | 12/1998 | Emerich et al. |
| 5,873,849 A | 2/1999 | Bernard |
| 5,921,245 A | 7/1999 | O'Donnell, Jr. |
| 5,938,688 A | 8/1999 | Schiff |
| 5,975,085 A | 11/1999 | Rise |
| 5,978,702 A | 11/1999 | Ward et al. |
| 6,015,786 A | 1/2000 | Mascarenhas et al. |
| 6,016,449 A | 1/2000 | Fischell et al. |
| 6,036,459 A | 3/2000 | Robinson |
| 6,042,579 A | 3/2000 | Elsberry et al. |
| 6,051,017 A | 4/2000 | Loeb et al. |
| 6,093,180 A | 7/2000 | Elsberry |
| 6,094,598 A | 7/2000 | Elsberry et al. |
| 6,128,537 A | 10/2000 | Rise |
| 6,129,685 A | 10/2000 | Howard, III |
| 6,132,361 A | 10/2000 | Epstein et al. |
| 6,161,045 A | 12/2000 | Fischell et al. |
| 6,176,242 B1 | 1/2001 | Rise |
| 6,216,030 B1 | 4/2001 | Howard et al. |
| 6,227,203 B1 | 5/2001 | Rise et al. |
| 6,230,049 B1 | 5/2001 | Fischell et al. |
| 6,248,126 B1 | 6/2001 | Lesser et al. |
| 6,251,115 B1 | 6/2001 | Williams et al. |
| 6,251,669 B1 | 6/2001 | Luskin |
| 6,263,237 B1 | 7/2001 | Rise |
| 6,278,895 B1 | 8/2001 | Bernard |
| 6,353,754 B1 | 3/2002 | Fischell et al. |
| 6,353,762 B1 | 3/2002 | Baudino et al. |
| 6,366,813 B1 | 4/2002 | DiLorenzo |
| 6,399,574 B1 | 6/2002 | McCabe et al. |
| 6,418,344 B1 | 7/2002 | Rezai et al. |
| 6,425,852 B1 | 7/2002 | Epstein et al. |
| 6,463,328 B1 | 10/2002 | John |
| 6,473,639 B1 | 10/2002 | Fischell et al. |
| 6,514,937 B1 | 2/2003 | Mascarenhas |
| 6,539,263 B1 | 3/2003 | Schiff et al. |
| 6,567,696 B2 | 5/2003 | Voznesensky et al. |
| 6,591,138 B1 | 7/2003 | Fischell |
| 6,592,509 B1 | 7/2003 | Hunter, Jr. |
| 6,594,880 B2 | 7/2003 | Eisberry |
| 6,597,954 B1 | 7/2003 | Pless et al. |
| 6,609,030 B1 | 8/2003 | Rezai et al. |
| 6,609,031 B1 | 8/2003 | Law et al. |
| 6,620,151 B2 | 9/2003 | Blischak et al. |
| 6,629,973 B1 | 10/2003 | Wardell et al. |
| 6,666,845 B2 | 12/2003 | Hooper et al. |
| 6,708,064 B2 | 3/2004 | Rezai |
| 6,712,753 B2 | 3/2004 | Manne |
| 6,735,474 B1 | 5/2004 | Loeb et al. |
| 6,735,475 B1 | 5/2004 | Whitehurst et al. |
| 6,782,292 B2 | 8/2004 | Whitehurst |
| 6,819,956 B2 | 11/2004 | DiLorenzo |
| 6,871,098 B2 | 3/2005 | Nuttin et al. |
| 6,898,455 B2 | 5/2005 | Anderson et al. |
| 6,907,280 B2 | 6/2005 | Becerra et al. |
| 7,010,351 B2 | 3/2006 | Firlik et al. |
| 7,104,947 B2 | 9/2006 | Riehl |
| 7,107,097 B2 | 9/2006 | Stern et al. |
| 7,346,395 B2 | 3/2008 | Lozano et al. |
| 7,353,065 B2 | 4/2008 | Morrell |
| 2002/0058867 A1 | 5/2002 | Breiter et al. |
| 2002/0062143 A1 | 5/2002 | Baudino et al. |
| 2002/0091419 A1 | 7/2002 | Firlik |
| 2002/0169485 A1 | 11/2002 | Pless et al. |
| 2003/0028072 A1 | 2/2003 | Fischell et al. |
| 2003/0032001 A1 | 2/2003 | Broderick |
| 2003/0097159 A1 | 5/2003 | Schiff et al. |
| 2003/0149457 A1 | 8/2003 | Tcheng et al. |
| 2003/0181954 A1 | 9/2003 | Rezai |
| 2004/0092010 A1 | 5/2004 | Ruiz I Altaba et al. |
| 2004/0172091 A1 | 9/2004 | Rezai |
| 2004/0186532 A1 | 9/2004 | Tadlock |
| 2005/0021118 A1 | 1/2005 | Genau et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0143799 A1 | 6/2005 | Black et al. |
| 2005/0143800 A1 | 6/2005 | Lando et al. |
| 2006/0004422 A1* | 1/2006 | De Ridder ............. 607/45 |
| 2006/0015153 A1 | 1/2006 | Gliner et al. |
| 2006/0106430 A1 | 5/2006 | Fowler et al. |
| 2006/0212090 A1 | 9/2006 | Lozano et al. |
| 2006/0212091 A1 | 9/2006 | Lozano et al. |
| 2006/0259094 A1 | 11/2006 | Naisberg et al. |
| 2007/0203545 A1 | 8/2007 | Stone et al. |
| 2007/0244519 A1 | 10/2007 | Keacher et al. |
| 2007/0265489 A1 | 11/2007 | Fowler et al. |
| 2008/0103548 A1 | 5/2008 | Fowler et al. |
| 2008/0208285 A1 | 8/2008 | Fowler et al. |
| 2010/0057159 A1 | 3/2010 | Lozano |

FOREIGN PATENT DOCUMENTS

| | | |
|---|---|---|
| WO | WO 03043690 | 5/2003 |
| WO | WO 03063951 | 8/2003 |

OTHER PUBLICATIONS

Ketter, et al., "Functional Brain Imaging, Limbic Function, and Affective Disorders," The Neuroscientist, vol. 2, No. 1, 1006, pp. 55-65.

Mayberg et al., "Reciprocal Limbic-Cortical Function and Negative Mood: Converging PET Findings in Depression and Normal Sadness," Am. J. Psychiatry 156:May 5, 1999, pp. 675-682.

Mayberg et al., "Regional Metabolic Effects of Fluoxetine in Major Depression: Serial Changes and Relationship to Clinical Response," Biological Psychiatry vol. 48, 2000, pp. 830-843.

Mayberg, "Frontal lobe dysfunction in secondary depression," J. Neuropsychiatry Clin. Neurosci., 6(4): 428-42, 1994.

Mayberg, Helen, "Modulating Dysfunctional Limbic-Cortical Circuits in Depression: towards development of brain-based algorithms for diagnosis and optimised treatment," British Medical Bulletin vol. 65, 2003, pp. 193-207.

Mayberg, Helen; "Limbic Cortical Dysregulation: A Proposed Model of Depression," Journal of Neuropsychiatry vol. 9 No. 3, 1997, pp. 471-481.

U.S. Appl. No. 12/139,392, filed Jun. 13, 2008, Sloan.

Al-Hakim, et al. "A Dorsolateral Prefrontal Cortex Semi-Automatic Segmenter," Proceedings of the SPIE Medical Imaging 2006; 6144:170-177.

Boisgueheneuc, et al. "Functions of the left superior frontal gyrus in humans: a lesion study", Brain, Oxford University Press. Advance Access publication Sep. 1, 2006, pp. 3315-3328.

Herwig, et al. "Antidepressant effects of augmentative transcranial magnetic stimulation", British Journal of Psychiatry, Nov. 2007, pp. 441-448.
Holmes, et al. "Spatiotemporal Dynamics of Error Processing Dysfunctions in Major Depressive Disorder", Arch Gen Psychiatry, vol. 65, No. 2, Feb. 2008, 10 pages.
International Search Report and Written Opinion; International Application No. PCT/US08/85973; Filed Dec. 8, 2008; Applicant: Northstar Neuroscience, Inc.; Mailed Jan. 26, 2009; 15 pages.
Kido, et al. "Computed Tomographic Localization of the Precentral Gyrus", Neuroradiology, May 1980, 5 pages.
Lozano, et al. "Subcallosal Cingulate Gyrus Deep Brain Stimulation for Treatment-Resistant Depression", Priority Communication, Notice in the Press, Society of Biological Psychiatry. Copyright 2008, 7 pages.
Ongur, et al. "The Organization of Networks within the Orbital and Medial Prefrontal Cortex of Rats, Monkeys, and Humans", Cerebral Cortex, Mar. 2000, vol. 10., pp. 206-219.
Petries, et al. "Dorsolateral prefrontal cortex: comparative cytoarchitectonic analysis in the human and the macaque brain and corticocortical connection patterns", European Journal of Neuroscience, vol. 1, pp. 1011-1036, 1999.
Rajkowska, et al. "Cytoarchitectonic Definition of Prefrontal Areas in the Normal Human Cortex: II. Variability in Locations of Area 9 and 46 and Relationship to the Talairach Coordinate System", Cerebral Cortex, Jul./Aug. 1995, pp. 323-337.
Volz, et al. "Why am I unsure? Internal and external attributions of uncertainty dissociated by fMRI", NeuroImage 21 (2004), pp. 848-847.
Bremner, et al., "Reduced volume of orbitofrontal cortex in major depression," Biological Psychiatry, Feb. 2002, 51:4, 273-279.
Quirk, et al., "Stimulation of medial prefrontal cortex decreases the responsiveness of central amygdala output neurons," The Journal of Neuroscience, 2003, 23(25): 8800-8807.
Shin, et al., "A Functional Magnetic Resonance Imaging Study of Amygdala and Medial Prefrontal Cortex Responses to Overly Presented Fearful Faces in Posttraumatic Stress Disorder," Arch en Psychiatry, vol. 62, Mar. 2005, 273-281.
Barbas et al. "Topographically Specific Hippocampal Projections Target Functionally Distinct Prefrontal Areas in the Rhesus Monkey," Hippocampus vol. 5, 1995, pp. 511-533.
Barbas et al., "Projections from the Amygdala to Basoventral and Mediodorsal Prefrontal Regions in the Rhesus Monkey," The Journal of Comparative Neurology, vol. 300, 1990, pp. 549-571.
Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).
Bjorklund et al., "Cell replacement therapies for central nervous system disorders," Commentary, Nature Neuroscience, vol. 3, No. 6, Jun. 2000, pp. 537-544.
Bremner, J.D., "Structural Changes in the Brain in Depression and Relationship to Symptom Recurrence," CNS Spectrums, vol. 7, No. 2 Feb. 2002, pp. 129-139.
Budson et al., "Memory Dysfunction," N. Eng. J. Med., 352(7): 692-699, 2005.
Caetano et al., "Anatomical MRI Study of Hippocampus and Amygdalia in Patients with Current and Remitted Major Depression," Psychiatry Research: Neuroimaging vol. 132, 2004, pp. 141-147.
Capel et al, "The influence of electrostimulation on hexobarbital induced loss of righting reflex in rats," Acupunct Electrother. Res. 7(1): 17-26, 1982.
Cosgrove et al. "Psychosurgery," Neurosurgery Clinicals of North America vol. 6 No. Jan. 1995. pp. 167-176.
Delbello et al., "Magnetic Resonance Imaging Analysis of Amygdala and other Subcortical Brain Regions in Adolescents with Bipolar Disorders," Bipolar Disorders vol. 6, 2004, pp. 43-52.
Diamond et al., "Preclinical Research on Stress, Memory and the Brain in the Development of Pharmacotherapy for Depression," European Neuropsychopharmacology vol. 14, 2004 pp. S491-S495.
Dougherty et al., "Cerebral metabolic correlates as potential predictors of response to anterior cingulotomy for treatment of major depression," J. Neurosurg., 99(6): 1010-7, 2003.

Drevets et al. "Functional Anatomical Correlates of Antidepressants Drug Treatment Assessed Using PET Measures of Regional Glucose Metabolism," European Neuropsychopharmology vol. 12, 2002, pp. 527-544.
Drevets et al. "Subgenal Prefrontal Cortex Abnormalities in Mood Disorders," Nature vol. 386, Apr. 24, 1997, pp. 824-827.
Ebmeier et al. "Cerebral Perfusion Correlates of Depressed Mood," British Journal of Psychiatry vol. 178, 1997, pp. 77-81.
Fossati et al., "Neuroplasticity: from MRI to Depressive Symptoms," European Neuropsychophamacology vol. 14, 2004, pp. S503-S510.
Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).
Galynker et al. "Hypofrontality and Negative Symptoms in Major Depressive Disorder," The Journal of Nuclear Medicine vol. 39, No. 4, Apr. 1998, pp. 608-612.
Goldapple et al., "Modulation of Cortical-Limbic Pathways in Major Depression," Arch Gen Psychiatry, vol. 61, Jan. 2004, pp. 34-41.
Gordon et al., "Parameters for direct cortical electrical stimulation in the human: histopathologic confirmation," Electroencephalography and clinical Neurophysiology, vol. 75, pp. 371-377 (1990).
Haberler et al., "No Tissue Damage by Chronic Deep Brain Stimulation in Parkinson's Disease," Annals of Neurology, vol. 48, No. 3, Sep. 2000, pp. 372-376.
Haldane et al., "New Insights Help Define the Pathophysiology of Bipolar Affective Disorder: Neuroimaging and Neuropathology Findings," Progress in Neuro-Psychopharmacology & Biological Psychiatry, vol. 28, 2004, pp. 943-960.
Hilty et al., "A Review of Bipolar Disorder Among Adults," Psychiatric Services vol. 50, 1999, pp. 201-213.
Huerta et al., "Low-Frequency Stimulation at the Troughts of 0-Oscillation Induces Long-Term Depression of Previously Potentiated CA1 Synapses," Journal of Neurophysiology vol. 75, No. 2, Feb. 1996, pp. 877-884.
Jimenez et al., "A Patient with a Resistant Major Depression Disorder Treated with Deep Brain Stimulation in the Inferior Peduncle," Neurosurgery, 57(3): 585-593, 2005.
Keightley et al., "An fMRI study investigating cognitive modulation of brain regions associated with emotional processing of visual stimuli," Neuropsychologia, 41(5): 585-96, 2003.
Keightley et al., "Personality influences limbic-cortical interactions during sad mood induciton," Neuroimage, 20(4): 2031-9, 2003.
Lange et al., "Enlarged Amygdala Volume and Reduced Hippocampal Volume in Young Women with Major Depression," Psychological Medicine vol. 34, 2004, pp. 1059-1064.
Liotti et al., "The role of functional neuroimaging in the neuropsychology of depression," J. Clin. Exp. Neuropsychol., 23(1): 121-36, 2001.
Liotti et al., "Differential Limbic-Cortical Correlates of Sadness and Anxiety in Healthy Subjects: Implications for Affective Disorders," Society of Biological Psychiatry, vol. 48, 2000, pp. 30-42.
Liotti et al., "Unmasking disease-specific cerebral blood flow abnormalities: mood challenge in patients with remitted unipolar depression," Am. J. Psychiatry, 159(11): 1830-40, 2002.
Little et al., "How Common is Resistance to Treatment in Recurrent, Nonpsychotic Geriatric Depression?", American Journal of Psychiatry 155: 8, Aug. 1998, pp. 1035-1038.
Mayberg et al., "Cingulate function in depression: a potential predictor of treatment response," Neuroreport, 8(4): 1057-61, 1997.
Mayberg et al., "Clinical correlates of PET- and SPECT-identified defects in dementia," J. Clin Psychiatry, 55 Suppl.: 12-21, 1994.
Mayberg et al., "Deep brain stimulation for treatment-resistant depression," Neuron, 45(5): 651-60, 2005.
Mayberg et al., "Depression in Parkinson's disease: a biochemical and organic viewpoint," Adv. Neurol., 65: 49-60, 1995.
Mayberg et al., "Paralimbic frontal lobe hypometabolism in depression associated with Huntington's disease," Neurology, 42(9): 1791-7, 1992.
Mayberg et al., "Paralimbic hypoperfusion in unipolar depression," J. Nucl. Med., 35(6):929-34, 1994.
Mayberg et al., "Selective hypometalbolism in the inferior frontal lobe in depressed patients with Parkinson's disease," Ann Neurol., 28(1): 57-64, 1990.

Mayberg et al., "The Functional Neuroanatomy of the Placebo Effect," American Journal of Psychiatry vol. 159, 2002, pp. 728-737.
Mayberg, "Depression, II: localization of pathophysiology," Am. J. Psychiatry, 159(12): 1979, 2002.
Mayberg, "Position emission tomography imaging in depression: a neural systems perspective," Neuroimaging Clin. N. Am., 13(4): 805-15, 2003.
Mayberg, Helen, "Modulating Limbic-Cortical Circuits in Depression: Targets of Antidepressant Treatments," Seminars in Clinical Neuropsychiatry vol. 7, No. 4, Oct. 2002, pp. 255-268.
Patterson et al., "Electrostimulation: addiction treatment for the coming millennium," J. Altern. Complement Med., 2(4): 485-91, 1996.
Patterson et al., "Neuro-electric therapy: criticisms of the 1984 Bethlem Study," Br. J. Addict., 84(7): 818, 1989.
Patterson, "Effects of neuro-electric therapy (N.E.T.) in drug addiction: interim report," Bull. Narc. 28(4): 55-62, 1976.
Patterson, "Electrostimulation and opiate withdrawal," Br. J. Psychiatry, 146-213. 1985.
Patterson, "Electrotherapy: addictions and neuroelectric therapy," Nurs. Times, 75(48): 2080-3, 1979.
Philips et al., "Neurobiology of Emotion Perseption I: The Neural Basis of Normal Emotion Perception," Bio Psychiatry vol. 54, 2003, pp. 515-528.
Philips et al., "Neurobiology of Emotion Perseption II: Implications for Major Psychiatric Disorders," Biol Psychiatry vol. 54, 2003, pp. 515-528.
Rauch, S. L., "Neuroimaging and Neurocircuitry Models Pertaining to the Neurosurgical Treatment of Psychiatry Disorders," Neurosurg Clin N. Am., vol. 14, 2003, pp. 213-223.
Sander et al., "The Human Amygdala: An Evolved System for Relevance Detection," Reviews in Neuroscience vol. 14, 2003, pp. 303-316.
Semniowicz et al., "Limbic-frontal Circuitry in Major Depression: A Path Modeling Metanalysis," NeuroImage vol. 22, 2004, pp. 409-418.
Sheline, Yvette, "3D MRI Studies of Neuroanatomic Changes in Unipolar Major Depression: The Role of Stress and Medical Comorbidity," Biol Psychiatry, vol. 48, 2000, pp. 791-800.
Soares et al., "The Functional Neuroanatomy of Mood Disorders," J. Psychiat. Res., vol. 31, No. 4, 1997, pp. 393-432.
Starkstein et al., "Depression and cognitive impairment in Parkinson's disease," Brain. 112 (Pt. 5) 1141-53, 1989.
Stefurak et al., "Deep brain stimulation for Parkinson's disease dissociates mood and motor circuits: a functional MRI case study," Mov. Disord., 18(12): 1508-16, 2003.
Temple, "Stem cell plasticity—building the brain of our dreams," Perspectives, Nature Reviews—Neuroscience vol. 2, Jul. 2001, pp. 513-520.
Velasco et al., "Neurobiological Background for Performing Surgical Intervention in the Inferior Thalmic Peduncle for Treatment of Major Depression Disorders," Neurosurgery, 57(3): 439-448, 2005.
Videbech et al., "Hippocampal Volume and Drepression: A Meta-Analysis of MRI Studies," Am. J. Psychiatry vol. 161, No. 11, Nov. 2004, pp. 1957-1966.
Weissmen et al., "Cross-National Epidemiology of Major Depression and Bipolar Disorder," JAMA vol. 276, No. 4, Jul. 24/31, 1996, pp. 293-299.
International Search Report for PCT/US2008/085973 dated Dec. 8, 2008.

* cited by examiner

SYSTEMS AND METHODS FOR PROVIDING TARGETED NEURAL STIMULATION THERAPY TO ADDRESS NEUROLOGICAL DISORDERS, INCLUDING NEUROPYSCHIATRIC AND NEUROPYSCHOLOGICAL DISORDERS

CROSS-REFERENCE TO RELATED APPLICATIONS

This application claims the benefit of and priority to U.S. Provisional Application 61/012,389, filed Dec. 7, 2007; U.S. Provisional Application 61/086,203, filed Aug. 5, 2008; U.S. Provisional Application 61/091,324, filed Aug. 22, 2008; and U.S. Provisional Application 61/105,747, filed Oct. 15, 2008, each of which is incorporated herein in its entirety by reference. This application further relates to U.S. Patent Application Publication No. 20070265489, entitled "Methods for Establishing Parameters for Neural Stimulation, Including via Performance of Working Memory Tasks, and Associated Kits," filed on Apr. 19, 2007; and U.S. Patent Application Publication No. 20080103548, entitled "Methods for Treating Neurological Disorders, Including Neuropsychiatric and Neuropsychological Disorders, and Associated Systems," filed Aug. 2, 2007, each of which is incorporated herein in its entirety by reference.

TECHNICAL FIELD

Aspects of the present disclosure are directed generally toward systems and methods for providing targeted delivery of extrinsic stimulation signals to treat neurological disorders, including neuropsychiatric and neuropsychological disorders.

BACKGROUND

A wide variety of mental and physical processes are controlled or influenced by neural activity in particular regions of the brain. For example, the neural functions in some areas of the brain (i.e., the sensory or motor cortices) are organized according to physical or cognitive functions. Several areas of the brain appear to have distinct functions in most individuals. In the majority of people, for example, the areas of the occipital lobes relate to vision, the regions of the left inferior frontal lobes relate to language, and particular regions of the cerebral cortex appear to be consistently involved with conscious awareness, memory, and intellect.

Many problems or abnormalities can be caused by damage, disease and/or disorders in the brain. Disorders include neuropsychiatric and/or neuropsychological disorders, such as major depressive disorder (MDD). A person's neuropsychiatric state may be controlled by particular cortical structures, subcortical structures, and/or signal pathways between such structures.

Neurological problems or abnormalities are often related to electrical and/or chemical activity in the brain. Neural activity is governed by electrical impulses or "action potentials" generated in neurons and propagated along synaptically connected neurons. When a neuron is in a quiescent state, it is polarized negatively and exhibits a resting membrane potential typically between −70 and −60 mV. Through chemical connections known as synapses, any given neuron receives excitatory and inhibitory input signals or stimuli from other neurons. A neuron integrates the excitatory and inhibitory input signals it receives, and generates or fires an action potential when the integration exceeds a threshold potential. A neural firing threshold, for example, may be approximately −55 mV.

When electrical activity levels are irregular, action potentials may not be generated in a normal manner. For example, action potentials may be generated too frequently, or not frequently enough. Such irregularities can result in neurologic dysfunction. It follows, then, that neural activity in the brain can be influenced by electrical energy supplied from an external source, such as a waveform generator. Various neural functions can be promoted or disrupted by applying an electrical current to the cortex or other region of the brain. As a result, researchers have attempted to treat physical damage, disease and disorders in the brain using electrical or magnetic stimulation signals to control or affect brain functions.

Transcranial electrical stimulation (TES) is one such approach that involves placing an electrode on the exterior of the scalp and delivering an electrical current to the brain through the scalp and skull. Another treatment approach, transcranial magnetic stimulation (TMS), involves producing a magnetic field adjacent to the exterior of the scalp over an area of the cortex. Yet another treatment approach involves direct electrical stimulation of neural tissue using implanted deep brain stimulation electrodes (DBS). However, the foregoing techniques may not consistently produce the desired effect with the desired low impact on the patient. For example, TES may require high currents to be effective, which may cause unwanted patient sensations and/or pain. TMS may not be precise enough to target only specific areas of the brain. Deep brain stimulation is a relatively invasive procedure, and it can be relatively difficult to implant DBS electrodes in tissue located well below the cortex. Accordingly, there exists a need for providing more effective, less invasive treatments for neuropsychiatric and neuropsychological disorders.

DETAILED DESCRIPTION

Introduction

Figure 1A:
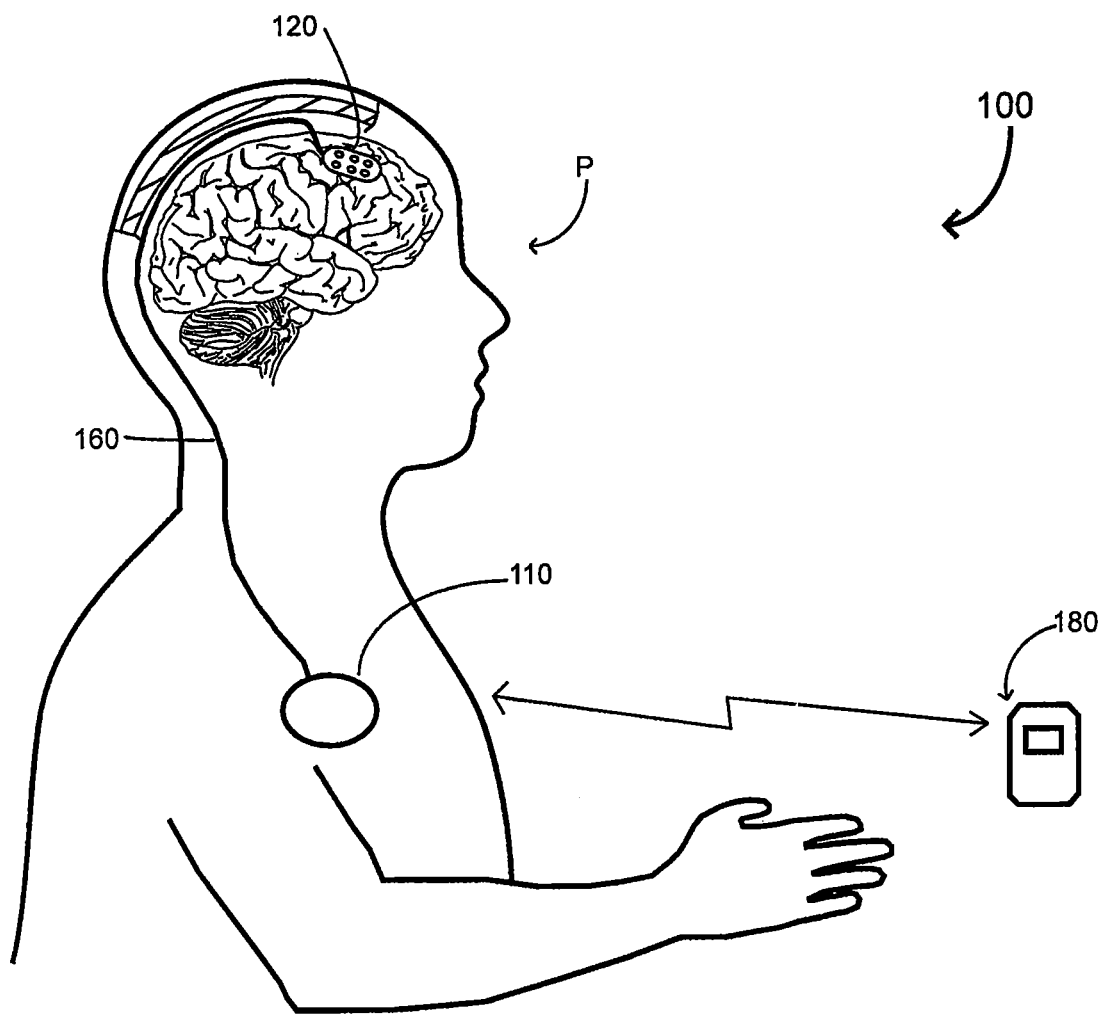
FIGS. 1A and 1B are schematic illustrations of representative neural stimulation systems in accordance with the present disclosure.

The present disclosure is directed to methods and systems for treating neurologic dysfunction, which may include neuropsychiatric, neuropsychological, neurodevelopmental and/or other disorders. As used herein, the phrase "neurologic dysfunction" is used to encompass a variety of conditions or disorders, including neuropsychiatric disorders and neuropsychological disorders. As a further shorthand, the term "neuropsychiatric disorders" is often used to include both neuropsychiatric disorders and neuropsychological disorders. Representative types of disorders falling within this definition include major depressive disorder (MDD), mania and other mood disorders, bipolar disorder, obsessive-compulsive disorder (OCD), Tourette's syndrome, schizophrenia, dissociative disorders, anxiety disorders, phobic disorders, post-traumatic stress disorder (PTSD), borderline personality disorder, as well as others such as Attention Deficit/Hyperactivity Disorder (ADHD) and/or craving or reward driven behaviors (e.g., associated with an addiction to legal or illegal drugs, gambling, sex, or another condition such as obesity).

Various aspects of the methods and systems disclosed herein are directed to treating neurological conditions or states with electrical stimulation, for instance, electromagnetic stimulation applied to particular cortical structures of the patient's brain (e.g., extradurally or subdurally). More particularly, various aspects of embodiments disclosed herein are directed to defining, identifying, or selecting a set of target or reference neuroanatomical locations at or relative to which one or more signal transfer devices can be implanted or positioned to provide or facilitate enhanced neural stimulation treatment efficacy for treating neuropsychiatric disorders.

To treat the neurological condition(s), the patient can be provided with a signal transfer device, e.g., a signal delivery device and/or a signal monitoring device. A given signal delivery device can include one or more portions of an electrode device or assembly configured to apply electromagnetic signals to one or more neural populations, and a given signal monitoring device can include or more portions of an electrode device or assembly configured to detect neuroelectric, thermal, and/or other signals generated by or corresponding to particular neural populations. Various types of signal delivery and/or signal monitoring device configurations can be selected by a practitioner depending upon embodiment details. As used herein, stimulation signals can include signals that have an excitatory or facilitatory effect on neurons at a target neural population, and signals that have an inhibitory effect on such neurons. The terms "first," "second," etc. are used herein to distinguish among elements and may have different meanings in different embodiments. These descriptors when used in the present Detailed Description may not have a one-to-one correspondence with the same descriptors used in the claims. In general and unless otherwise specified, the terms "about" and "approximately", when use to modify dimensions, refer to ±2 mm and more particularly, ±1 mm.

A method in accordance with a particular embodiment of the disclosure is directed to a patient identified as having at least one of a neuropsychological disorder and a neuropsychiatric disorder. The method includes implanting at least one stimulation electrode within the patient's skull cavity, outside a cortical surface of the patient's brain and at a location in a range of 15 mm to about 35 mm anterior to a precentral sulcus reference point. The precentral sulcus reference point is positioned at the precentral sulcus and at the patient's middle frontal gyrus and/or superior frontal gyrus. The method can further include treating the patient's disorder by applying electrical stimulation to the patient via the at least one stimulation electrode.

In a particular aspect of the foregoing embodiment, the stimulation electrode is one of the plurality of stimulation electrodes, and all of the active stimulation electrodes implanted within the patient's skull cavity are implanted outside the cortical surface of the patient's brain at the patient's middle frontal gyrus and/or superior frontal gyrus. The electrode is the posterior-most electrode within the patient's skull cavity outside a cortical surface of the patient's brain via which electrical stimulation is applied to the patient's brain. The at least one electrode can be at least 18 mm anterior to the precentral sulcus reference point and is positioned superior to a linear or curvilinear line that at least approximately bisects the middle frontal gyrus into a superior portion and an inferior portion. The precentral sulcus reference point is approximately at an intersection of the precentral sulcus and the linear or curvilinear line.

A method in accordance with another embodiment for treating a patient includes implanting first and second electrodes within the patient's skull cavity and outside a cortical surface of the patient's brain. The first electrode can be located at one of Brodmann areas 6, 8, 9, 9/8, 10, 46 and 9/46, and the second electrode can be located another of Brodmann areas 6, 8, 9, 9/8 10, 46 and 9/46. The method can further include treating the patient's disorder by applying electrical stimulation to the patient via the first and second electrodes.

A method in accordance with still another embodiment of the disclosure includes implanting first and second electrodes within a patient's skull cavity and outside a cortical surface of the patient's brain, with the first electrode being located at the frontal cortical lobe of the brain and with the second electrode being located at an auditory processing area of the brain. The patient's neuropsychological and/or neuropsychiatric disorder can be treated by applying stimulation to the patient via the first and second electrodes.

In still further embodiments, electrodes can be positioned relative to a coronal suture of the patient's skull. One such method, directed to a patient identified as having at least one of a neuropsychological disorder and a neuropsychiatric disorder, includes implanting at least one electrode within the patient's skull cavity, outside a cortical surface of the patient's brain, and at or anterior to a reference position in a range of about 2 mm to about 12 mm posterior to the coronal suture of the patient's skull. The patient's disorder is treated by applying electrical stimulation to the patient via the at least one electrode.

Other aspects of the disclosure are directed to computer-implemented methods for identifying target stimulation regions for treating a patient's neurological disorder. One such method includes receiving machine-readable data corresponding to an individual patient's brain structures and determining a set of transformation values correlating the individual patient's brain structures with brain structures of a standard brain atlas. The method can further include receiving input corresponding to a portion of a brain structure at which stimulation electrodes are to be positioned, and a target minimum distance from a target or reference anatomical structure, feature, location, or point. The input is referenced to one of the standard brain atlas and the individual patient's brain structures. The method still further includes, based at least in part on the transformation values, mapping the received input to be with reference to the other of the standard brain atlas and the individual patient's brain structures.

A computer-implemented method in accordance with yet another embodiment includes (based at least in part on efficacy data for multiple patients receiving electrical stimulation from geometrically similar multi-electrode devices for treatment of at least one of a neuropsychological disorder and a neuropsychiatric disorder), determining locating information for positioning a geometrically similar multi-electrode device in another individual patient. The locating information can include an orientation of the multi-electrode device and an offset distance between at least one electrode of the multi-electrode device and an anatomical brain feature or location. The locating information can correspond to an electrode device position expected to produce efficacious results in the individual patient. The method can further include applying the locating information to a standard brain atlas, determining a set of transformation values correlating the individual patient's brain structures with brain structures of the standard brain atlas, and, based at least in part on the transformation values, mapping the locating information to be with reference to the individual patient's brain structures.

Figure 1B:
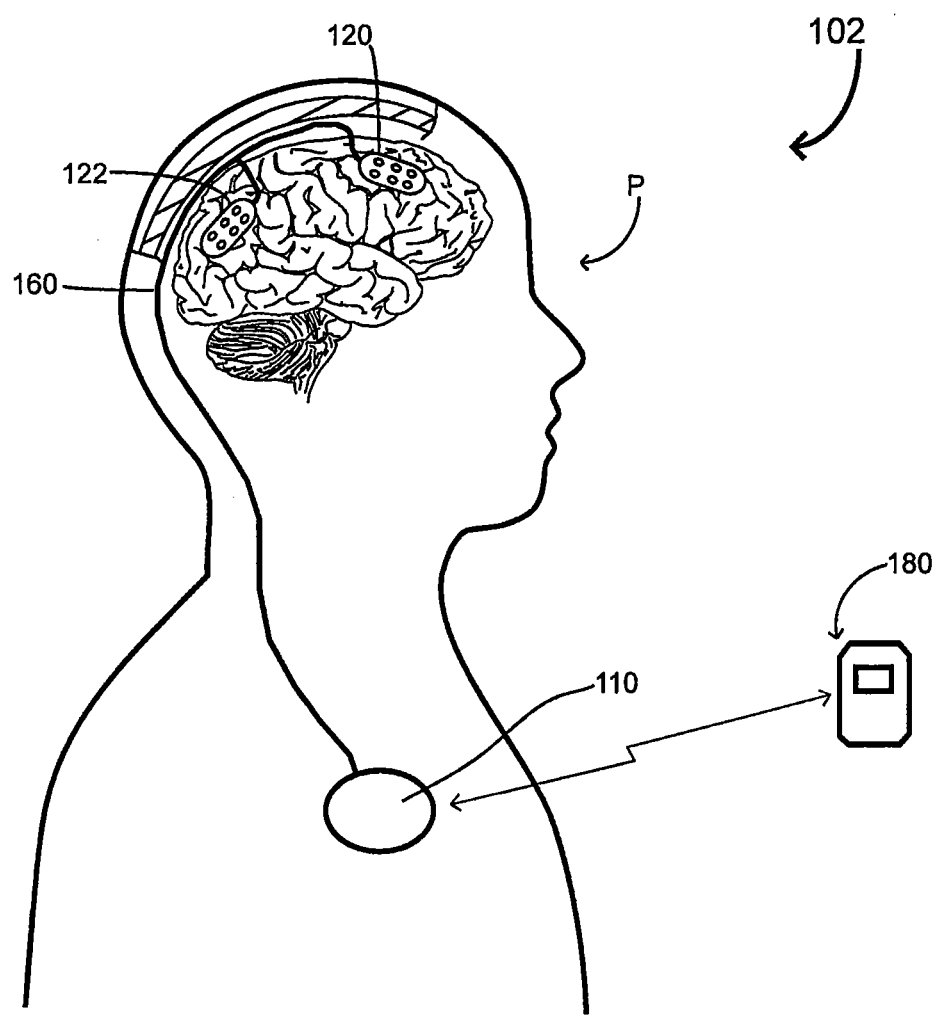

FIG. 1A is a schematic illustration of a representative neural stimulation system 100 configured in accordance with the present disclosure. In at least one embodiment, the neural stimulation system 100 includes a stimulation signal generator 110, which can be an implantable pulse generator (IPG). The system 100 can further include an electrode device 120 (or other signal delivery and/or detection device) implanted in the patient within the patient's skull cavity, a lead wire 160 that couples the IPG 110 and the electrode device 120, and an external programming and/or control unit 180. The external control unit 180 is configured for wireless signal communication with the IPG 110, so as to transfer commands, program instructions, queries, and data between the external control unit 180 and the IPG 110. FIG. 1B is a schematic illustration of another representative neural stimulation system 102 in accordance with the present disclosure, which includes first and second implanted electrode devices 120, 122.

The stimulation signal generator 110 shown in FIGS. 1A and 1B can be programmed to generate and output neural stimulation signals, such as electrical pulses having a pulse repetition frequency, a peak signal intensity or amplitude, a first-phase pulse width, pulse burst characteristics, and/or other stimulation signal parameters. Depending upon embodiment details, the stimulation signal generator 110 can output, for example, stimulation signals having a pulse repetition frequency between approximately 0.1 Hz and 500 Hz (e.g., approximately 0.1-250 Hz, or 10-150 Hz, or 25-125 Hz, or spanning a range that includes 50-100 Hz); a first-phase pulse width of between approximately 10-500 microseconds (e.g., 50-350, or 150-250 microseconds); a peak amplitude of approximately 1.0-20.0 mA (e.g., 5.0-15.0 mA); a bipolar or monopolar (anodal or cathodal) polarity; and a duty cycle between approximately 10%-100% (e.g., 25%, 50%, 75%, or 100%). In certain embodiments, the stimulation signal generator 110 can output signals having parameters that vary in an aperiodic or quasi-random manner at one or more times. The stimulation signals are applied or delivered to particular neural populations by the electrode device 120. In some embodiments, the stimulation signal generator 110 can be configured to receive or measure neuroelectric signals (e.g., electrocorticography (ECOG) signals) and/or other signals that are detected or sensed by the electrode device 120 or another sensor. In certain embodiments, the external control unit 180 can also be configured to receive, store, transfer, and/or analyze neuroelectric or other signals.

Figure 2A:
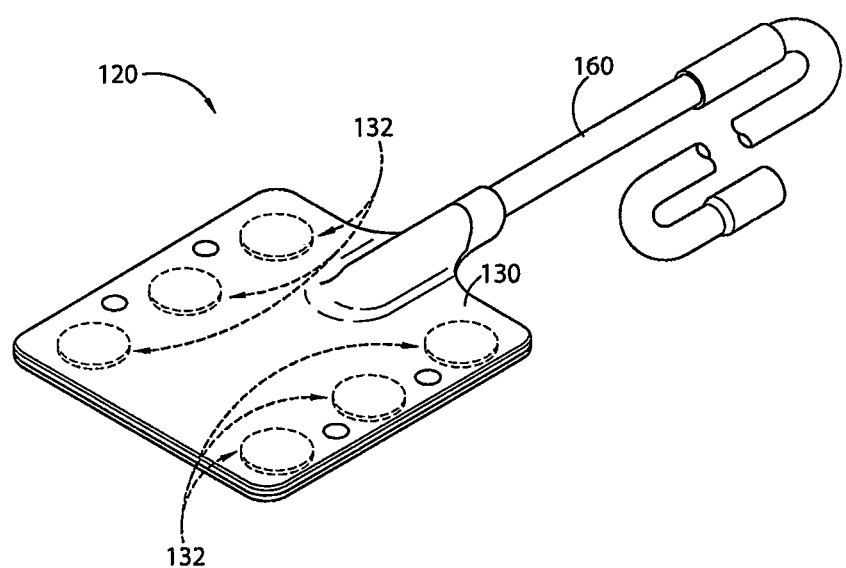
FIGS. 2A-2C are schematic illustrations of representative electrode devices in accordance with the present disclosure.

FIG. 2A is a schematic illustration of an electrode device 120 configured in accordance with an embodiment of the present disclosure. In general, the electrode device 120 includes a support member 130 (which can be generally planar) carrying least one electrode 132 that is electrically coupled to the stimulation signal generator 110 (e.g., by way of the lead wire 160). One or more of the electrodes 132 can be configured as a signal delivery device that can apply signals output by the stimulation signal generator 110 to neurons or neural structures (e.g., dendrites within a neural population that is beneath an electrode 132) residing adjacent or proximate to the electrode(s) 132. Additionally or alternatively, one or more of the electrodes 132 can be configured to operate as a signal monitoring device that can sense or detect neuroelectric signals generated by neurons or neural structures that reside adjacent or proximate to the electrode(s) 132. In certain embodiments, particular electrodes 132 can be configured to provide signal delivery functions and signal monitoring functions in an alternating or otherwise programmable manner.

Figure 2B:
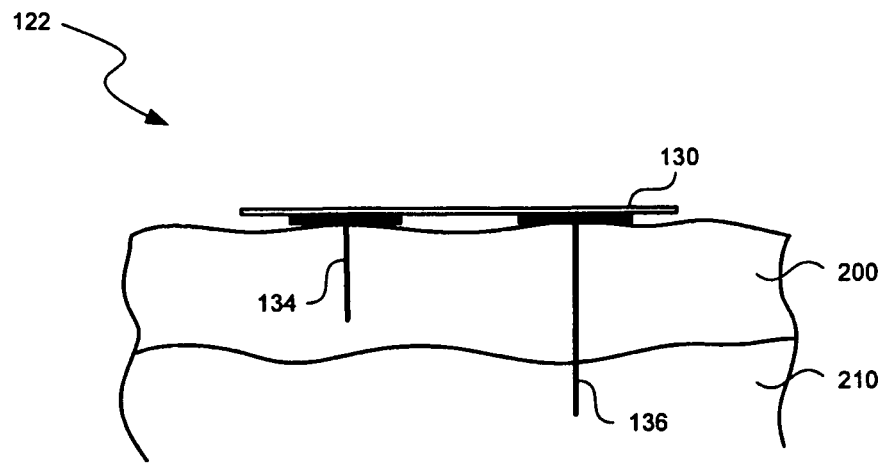
Figure 2C:
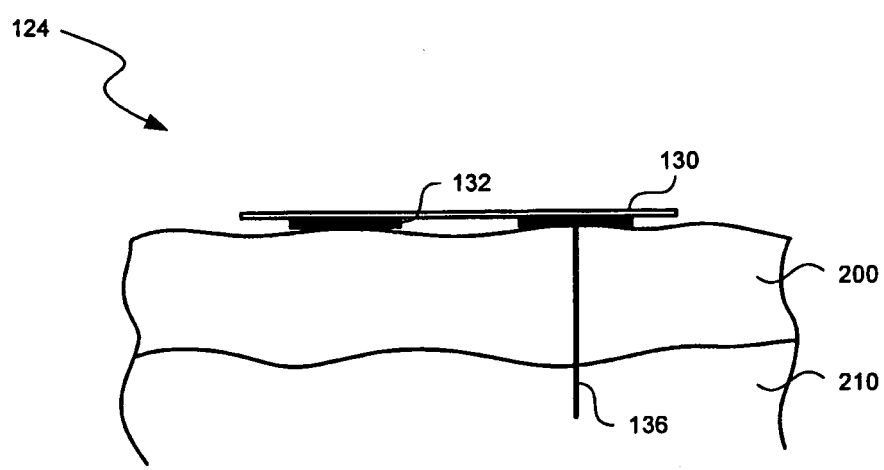

The electrode device 120 shown in FIG. 2A carries non-penetrating or surface electrodes. An electrode device 120 such as that shown in FIG. 2A can be implanted epidurally or subdurally outside the cortical surface to directly apply stimulation signals to neurons or neural structures that are located within an outer, more exterior, more superficial, or generally accessible portion of the brain. In other embodiments, the electrode device can carry one or more penetrating, needle-type, or probe-like electrodes or electrode structures. FIG. 2B is a schematic illustration of a representative electrode device 122 in accordance with the present disclosure, in which a support member 130 carries first and second penetrating or needle-type electrodes 134, 136. In the embodiment shown, the first penetrating electrode 134 can be configured to apply stimulation signals directly to intra-cortical tissue 200, while the second penetrating electrode 136 can be configured to apply stimulation signals directly to subcortical tissue 210. FIG. 2C is a schematic illustration of another representative electrode device 124 configured in accordance with the present disclosure, in which a support member 130 carries a set of surface or non-penetrating electrodes 132 as well as a set of intra-cortical and/or subcortical penetrating electrodes 136.

In accordance with the present disclosure, particular aspects of a neural stimulation system (e.g., one or more portions of a stimulation signal generator and/or an electrode device) can be implemented in one or more manners described in 1) U.S. Patent Application Publication No. 20060015153, entitled "Systems and Methods for Enhancing or Affecting Neural Stimulation Efficiency and/or Efficacy"; 2) U.S. patent application Ser. No. 12/139,392, entitled "Microdevice-Based Electrode Assemblies and Associated Neural Stimulation Systems, Devices, and Methods"; 3) U.S.

Patent Application Publication No. 20050021118, entitled "Apparatuses and Systems for Applying Electrical Stimulation to a Patient," filed on Jun. 25, 2004; and 4) U.S. Pat. No. 7,107,097, entitled "Articulated Electrode Assembly," each of which is incorporated herein in its entirety by reference.

Cortical Region Considerations in View of Neuropsychiatric Disorders

Different techniques exist for specifying particular portions of the cortex that can contribute to neurologic dysfunction associated with neuropsychiatric disorders. For instance, subregions of the frontal cortex (e.g., the cortical portion of the frontal lobe) that can contribute to neuropsychiatric dysfunction include neural populations within portions of Brodmann area 9, Brodmann area 9/8, Brodmann area 46, Brodmann area 9/46, Brodmann area 10, Brodmann area 8, and/or Brodmann area 6. Other frontal regions of relevance to neuropsychiatric dysfunction can include Brodmann area 24 and Brodmann area 25. Any particular Brodmann area is defined by its cytoarchitectonic characteristics, and thus the boundaries, span, or extent of any given Brodmann area may vary from one individual to another.

In addition to the foregoing, portions of the orbitofrontal cortex (OFC) and the dorsolateral prefrontal cortex (DLPFC) have been implicated in neurologic dysfunction corresponding to neuropsychiatric disorders (e.g., MDD). In general, the OFC can be defined to span portions of Brodmann area 10. The DLPFC can be defined to include portions of Brodmann area 9, and also portions of Brodmann area 46 and Brodmann area 9/46. Brodmann area 9/46 can be defined as a transition or boundary region between Brodmann areas 9 and 46, in accordance with cytoarchitectonic studies performed by Rajkowska et al. as described in "Cytoarchitectonic Definition of Prefrontal Areas in Normal Human Cortex: II. Variability in Locations of Areas 9 and 46 and Relationship to the Talairach Coordinate System," *Cerebral Cortex*, July/August 1995; 5:323-327, incorporated herein in its entirety by reference. Other transitional Brodmann areas can also be defined or identified, such as Brodmann area 9/8.

With respect to the DLPFC, multiple manners of defining the extent of the DLPFC exist. For instance, a semi-automated manner of defining the DLPFC is described by Al-Hakim et al. in "A Dorsolateral Prefrontal Cortex Semi-Automatic Segmenter," *Proceedings of the SPIE Medical Imaging* 2006; 6144:170-177, incorporated herein in its entirety by reference. The DLPFC can alternatively be defined, for instance, to span an area that includes neural populations that are further dorsal (located in the direction of the interhemispheric fissure) than the area spanned by Al-Hakim's DLPFC definition (e.g., to include portions of the superior frontal gyrus); and/or in accordance with combined aspects of the Al-Hakim DLPFC definition and a Rajkowska based DLPFC definition.

Various aspects of the present disclosure are directed to defining, identifying, and/or selecting a set of reference neuroanatomical locations, sites, or points at or relative to which one or more portions of a signal delivery device can be implanted, positioned, and/or oriented to enhance the likelihood of effectively treating a neuropsychiatric disorder, where such reference neuroanatomical locations can be identified in a precise and consistent manner from one patient to another. As further detailed below, in particular embodiments certain reference neuroanatomical locations can be determined in association with one or more structural imaging procedures, which can involve Magnetic Resonance Imaging (MRI) or Computed Tomography (CT) procedures. One or more reference neuroanatomical locations can also be determined based upon a set of skull landmarks, such as the coronal suture.

Identification of Reference Neuroanatomical Location(s), Sites, Points, and/or Origins In accordance with various embodiments of the present disclosure, one or more signal delivery and/or signal monitoring devices can be implanted or positioned relative to particular neuroanatomical structures or landmarks in a manner that enhances the likelihood that a patient will favorably respond to neural stimulation intended to address a given type of neurologic function or dysfunction. For instance, a pre-surgical planning protocol and/or a surgical implantation protocol can specify that given portions, elements, or features of one or more signal transfer, delivery, or detection devices (e.g., an electrode 132 carried by an electrode device 120 such as that shown in FIG. 2A) should be implanted at or approximately at particular neuroanatomical locations that are defined relative to a set of minimum, target, and/or maximum distances from one or more reference neuroanatomical structures, landmarks, features, or points, in accordance with standard neuroanatomical reference directions. Such a surgical implantation protocol can additionally specify or imply one or more predetermined signal delivery device orientations and/or signal monitoring device orientations with respect to portions of the brain.

Due to the brain's convoluted topology and variations in such topology from one individual to another, a specific target location upon the brain's surface may be challenging to precisely and consistently identify across multiple individuals in the absence of at least one reference point or origin that can be reproducibly identified from one individual to another. Particular brain structures or landmarks that span a substantial neuroanatomical area or region, and/or which traverse a significant neuroanatomical distance, can typically be identified across multiple individuals, e.g., visually and/or in association with computer based procedures for analyzing neural imaging data. Such brain structures can include one or more of the interhemispheric fissure, the Sylvian fissure, the central sulcus, the precentral sulcus, the superior frontal sulcus, the superior frontal gyrus, the middle frontal gyrus, and/or other structures.

Particular portions, features, and/or aspects of such reproducibly identifiable brain structures can be identified or defined, and used to establish at least one reference point or origin relative to which a set of signal transfer devices can be implanted in a patient in a manner that is consistent or generally consistent from one patient to another.

During a human clinical trial conducted by Northstar Neuroscience (Northstar Neuroscience, Inc., Seattle, Wash.), cortical stimulation was applied to patients to treat MDD using a cortical surface electrode device. The electrode device had one row of two electrodes, where each electrode had a diameter of 3.75 mm, and a center-to-center separation distance between electrodes was 15 mm. The stimulation was initially applied in the form of anodal biphasic pulses having a pulse repetition frequency of 50 Hz, a first-phase pulse width of 150 microseconds, a peak amplitude of approximately 6.5 mA, and a 100% duty cycle. Depending upon clinical response, particular stimulation parameters could be varied (e.g., signal polarity could be changed to cathodal, and/or duty cycle could be reduced, for instance, to 80%, 50%, or 25%) in accordance with specified allowable ranges. As described in further detail below, in each patient, the electrode device was implanted to facilitate the application of stimulation signals to portions of the patient's middle frontal gyrus. The results from the clinical trial indicate that the therapeutic efficacy of cortical stimulation to treat MDD and/or other neuropsychiatric disorders depends significantly upon the particular middle frontal gyrus location(s) at which stimulation signals are applied.

Figure 3A:
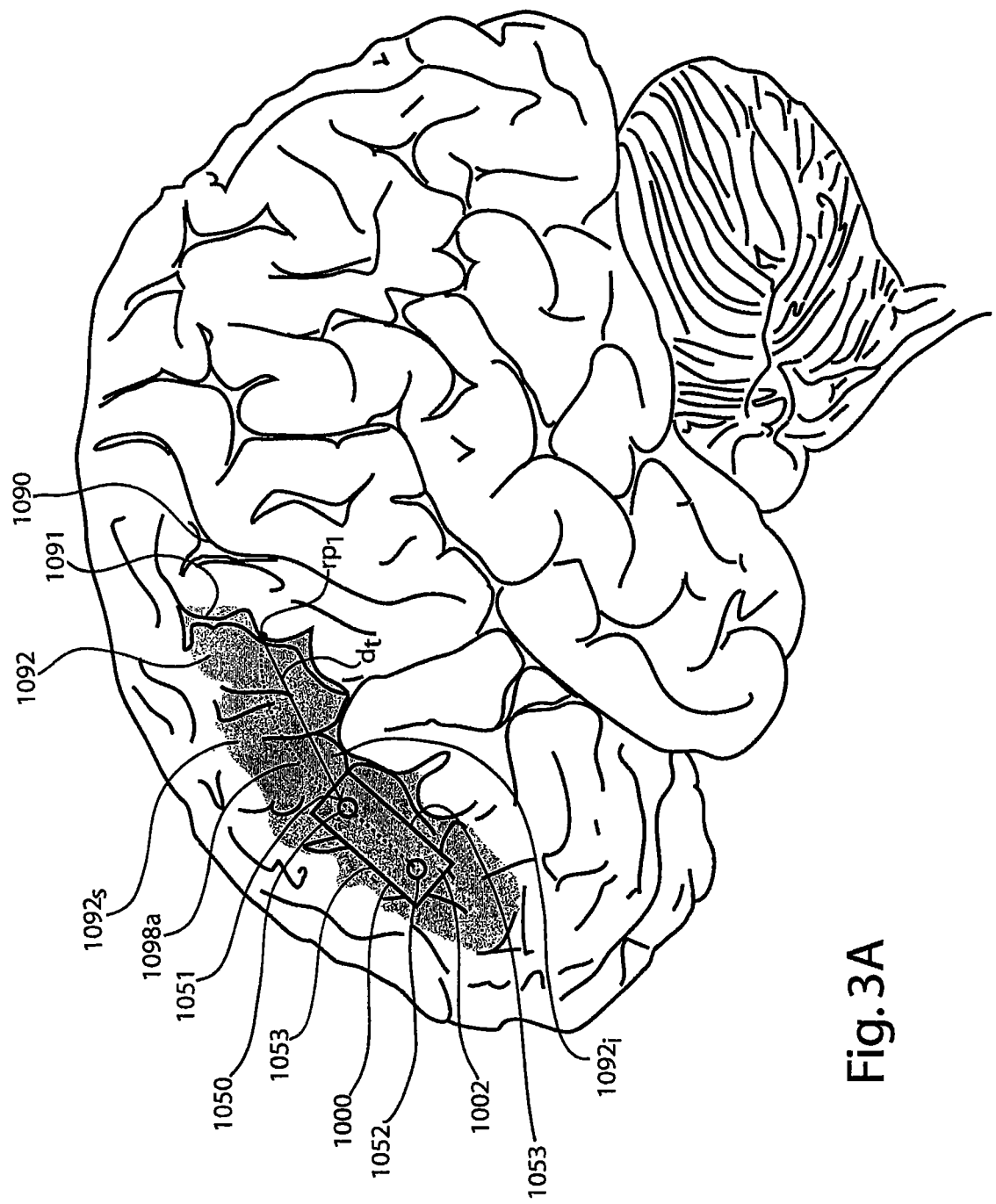
FIGS. 3A and 3B are schematic illustrations of an electrode device implanted above (e.g., epidurally) or upon (e.g., subdurally) a patient's middle frontal gyrus in accordance with an embodiment of the disclosure.

FIG. 3A is a graphical illustration of an electrode device 1000 implanted in a patient in accordance with an embodiment of the disclosure. In one embodiment, the electrode device 1000 includes a support member 1002 that carries a first electrode 1050 and a second electrode 1052. In this embodiment, each electrode 1050, 1052 is generally circular, although in other embodiments, the electrodes can have other shapes. In general, the manner in which FIG. 3A depicts the electrode device 1000 implanted above or upon the brain corresponds to a surgical protocol associated with the aforementioned clinical trial.

In general, the central sulcus 1090 and the precentral sulcus 1091 are reproducibly or repeatably identifiable neuroanatomical landmarks across multiple individuals. The precentral sulcus 1091 forms a posterior boundary or border of the middle frontal gyrus 1092. Thus, the posterior border or wall of the middle frontal gyrus 1092 can be defined to occur or exist along an anterior boundary of the precentral sulcus 1091. The middle frontal gyrus 1092 can be bisected, approximately bisected, or divided into a superior portion 1092s and an inferior portion 1092i by at least a segment of a middle frontal gyrus midline, bisecting arc, or dividing line, curve, or arc 1098a. In accordance with various embodiments of the present disclosure, one or more electrodes 1050, 1052 carried by the electrode device 1000 can be implanted to stimulate particular portions of the middle frontal gyrus 1092 in a manner that is expected to be reproducible from one patient to another, and which is expected to increase the likelihood that the applied stimulation signals provide adequate or efficacious therapeutic results for an acceptable percentage of patients or as many patients as possible. The electrodes can be implanted above the cortical surface (epidurally), upon the cortical surface (subdurally) or within the cortical surface (intra-cortically). In certain embodiments, one or more electrodes can be implanted below the cortical surface (subcortically).

As further described below, when treating neuropsychiatric disorders with extrinsic neural stimulation signals, therapeutic efficacy can be enhanced or improved when the stimulation signals are applied to neural populations within the middle frontal gyrus 1092 that reside at and/or anterior to a target minimum distance $d_t$ away from a neuroanatomical reference point, such as a point, location, or feature upon, defined by, or corresponding to a portion of the precentral sulcus 1091. Accordingly, much of the immediately following discussion relates to reference points defined relative to the precentral sulcus 1091. In certain situations, a reference point on the central sulcus 1090 may be easier to identify (e.g., visually from one or more MRI images) than a reference point on the precentral sulcus 1091, and therefore the central sulcus 1090 can also (e.g., additionally or alternatively) serve as an anatomical landmark from which $d_t$ is determined to facilitate increased consistency across implantation procedures performed by different neurosurgeons, and/or more predictable therapeutic results. Further details of techniques that reference the central sulcus 1090 are described later with reference to FIG. 5A.

The particular manner(s) in which the target minimum distance $d_t$ and/or the neuroanatomical reference point are defined can depend upon embodiment details. In the embodiment shown in FIG. 3A, a neuroanatomical reference point $rp_1$ is defined as a point at which the middle frontal gyrus midline 1098a intersects the posterior boundary of the middle frontal gyrus 1092 as defined by the precentral sulcus 1091. From a neuroanatomical perspective, the precentral sulcus 1091 has a given width (e.g., 0.5-1.5 mm). Thus, reference point $rp_1$ can additionally or alternatively be specified in an equivalent or generally equivalent manner by defining it as a point on the anterior side precentral sulcus 1091 at which the middle frontal gyrus midline 1098a and the precentral sulcus 1091 intersect. Furthermore, in some embodiments, reference point $rp_1$ can alternatively be specified in an approximately equivalent manner by defining it slightly more generally as a point on the precentral sulcus 1091 at which the middle frontal gyrus midline 1098a and the precentral sulcus 1091 intersect.

In one embodiment, the target minimum distance $d_t$ is defined as an anterior distance or offset between reference point $rp_1$ and the posterior edge of the posterior electrode 1050 when the electrode device 1000 is positioned such that the midpoint of the support member's posterior side is aligned or generally aligned with the midline 1098a of the middle frontal gyrus 1092. In another embodiment, the target minimum distance $d_t$ can be correspondingly defined as an anterior distance or offset between the reference point $rp_1$ and the posterior edge of the posterior electrode 1050 when the electrode device 1000 is positioned such that the posterior edge, midpoint, or approximate midpoint of the posterior electrode 1050 is aligned or generally aligned with the midline 1098a of the middle frontal gyrus 1092.

In various embodiments, the target minimum distance $d_t$ is defined as a curvilinear or approximately curvilinear distance along or above the brain surface. In some embodiments, the target minimum distance $d_t$ can be defined as a linear or piecewise linear distance along or above the brain surface. In general, to provide enhanced implantation accuracy and more consistent therapeutic results, the target minimum distance $d_t$ can be defined close or relatively close to the brain surface rather than along a portion of the cranium. The target minimum distance $d_t$ may be curvilinear rather than linear because the patient's brain surface is curved.

In general, depending upon the particular surgical implantation technique employed, the electrode device 1000 can be rotated so that the anterior electrode 1052 has any of a number of rotational orientations relative to the posterior electrode 1050. In order to facilitate consistent positioning of electrodes 1050, 1052 and/or electrode devices 1000 from one patient to another, in one embodiment the posterior edge 1051 of the electrode device's support member 1002 is implanted to be as perpendicular to the middle frontal gyrus midline 1098a as possible. Put another way, the electrodes 1050, 1052 or the long edges 1053 of the support member 1002 can be aligned to be parallel to the middle frontal gyrus midline 1098a. Additional orientation considerations relating to electrode device implantation are described below.

Figure 3B:
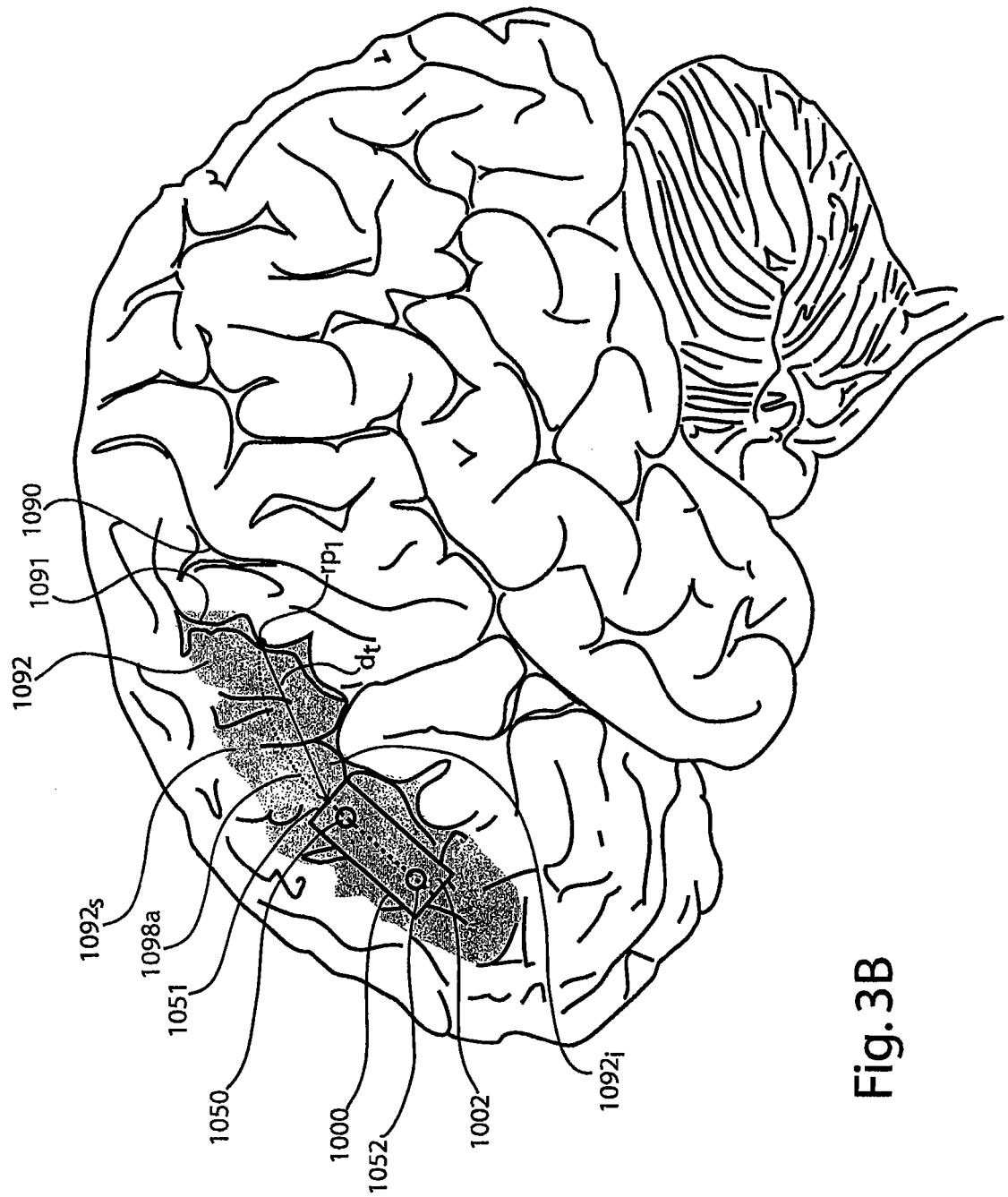

FIG. 3B is a graphical illustration of an electrode device 1000 implanted in a patient in accordance with another embodiment of the disclosure. In this embodiment, the origin or source location for specifying the target minimum distance $d_t$ is defined in the manner described above with reference to FIG. 3A, but the endpoint or terminus for specifying the target minimum distance $d_t$ is defined relative to the posterior edge 1051 of the support member 1002, rather than relative to the posterior electrode 1050. In such an embodiment, a separation distance between the particular support member boundary under consideration (e.g., the posterior edge 1051) and an outer edge or the approximate center of the posterior electrode 1050 under consideration should be taken into account to ensure that one or more most-posterior electrodes 1050 with which stimulation signals are applied are positioned at or anterior to the target distance that corresponds to increased or substantially increased therapeutic efficacy. Thus, in a representative example, if 1) therapeutic efficacy is enhanced when stimulation signals are applied approximately 20 mm or more anterior to a precentral sulcus reference point $rp_1$ defined with respect to the location at which the middle frontal gyrus midline 1098a intersects the precentral sulcus 1091; 2) a target minimum distance $d_t$ is specified relative to a midpoint along the width of the support member's posterior edge 1051; and 3) the separation distance between the midpoint along the width of the support member's posterior edge 1051 and the edge of the most-posterior electrode 1050 is approximately 5 mm, then the midpoint of the support member's posterior edge 1051 should be implanted approximately 15 mm or more anterior to reference point $rp_1$.

The offset or separation distance between the posterior edge 1051 of the support member 1002 and the center or an outer edge or periphery of a most posterior electrode 1050 is typically known. For example, this distance is typically a fixed, as-designed, as-manufactured distance that can be verified by measurement prior to implanting the electrode device. Thus, in accordance with an embodiment such as that representatively shown in FIG. 3B, a target minimum separation distance $d_t$ can be defined relative to an electrode device feature (such as a portion of a support member 1002), which conveys or implies specific and readily determinable separation distance information between a neuroanatomical reference point under consideration (e.g., reference point $rp_1$) and the location of a most posterior and/or other signal transfer device (e.g., the posterior electrode 1050 shown in FIG. 3B). In certain neurosurgical situations such as the implantation of an electrode device into a small burr hole, the definition of a target minimum separation distance $d_t$ relative to a portion of a support member 1002 may be more easily used by the practitioner than a distance measured relative to an electrode. Accordingly, using such a target distance can improve implantation consistency between neurosurgeons.

Figure 4B:
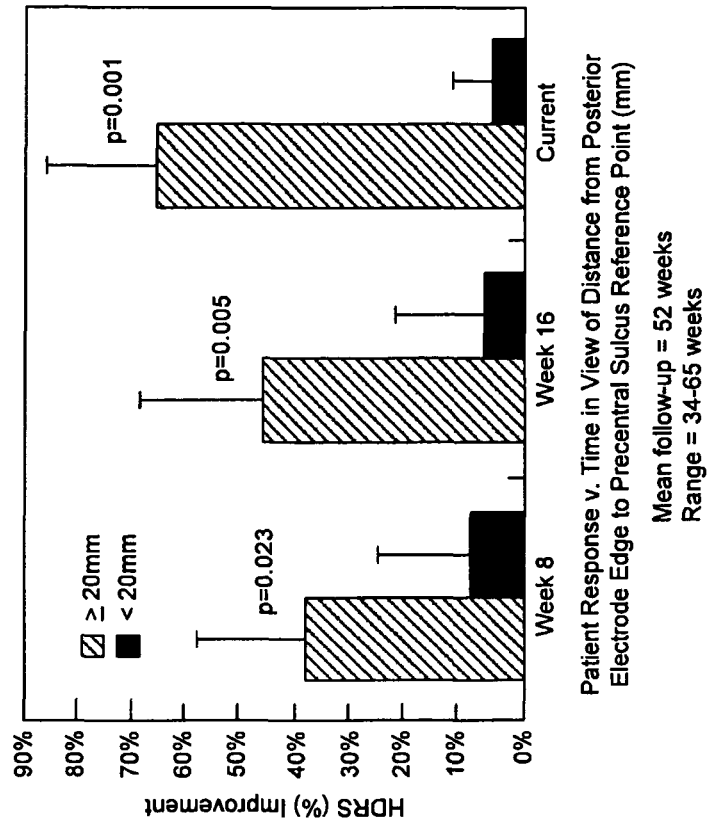
FIGS. 4A-4C are graphical illustrations of therapeutic results as a function of electrode implantation location obtained in association with a human clinical trial involving the application of cortical stimulation to treat MDD.
Figure 4A:
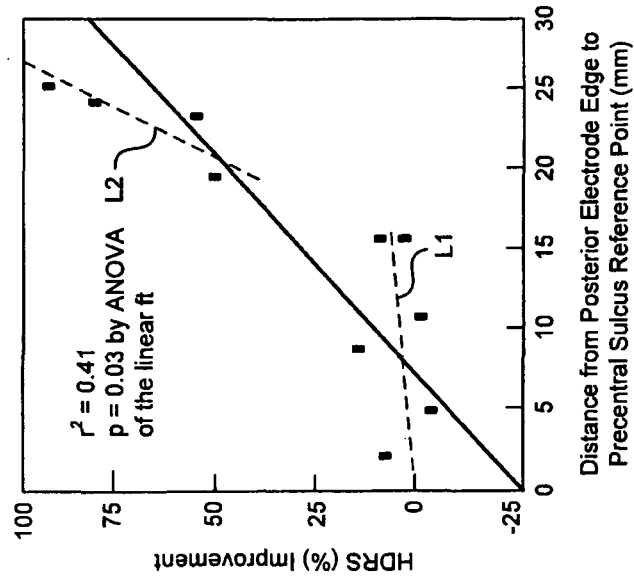
Figure 4C:
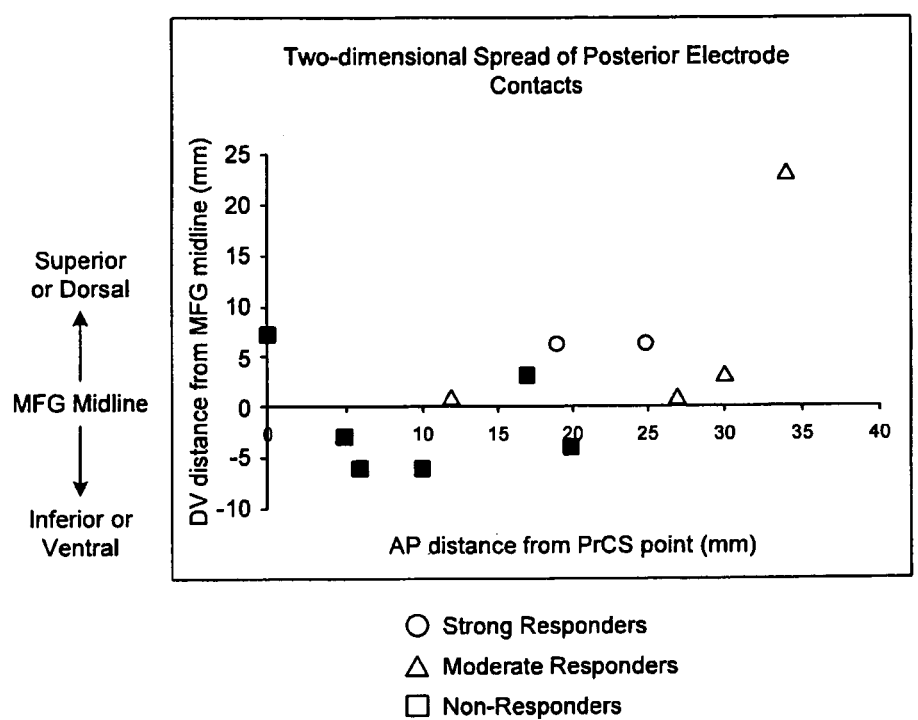

FIGS. 4A-4C graphically illustrate the therapeutic efficacy as a function of implanted electrode or electrode device location (or equivalently, stimulation signal application location) obtained during the aforementioned human clinical trial. FIG. 4A graphically indicates therapeutic efficacy as measured by the Hamilton Depression Rating Scale (HDRS) as a function of the distance between the most posterior edge of the posterior electrode 1050 and a precentral sulcus reference point $rp_1$. In this embodiment, the reference point $rp_1$ is the point or location on the anterior boundary of the precentral sulcus 1091, or equivalently, the posterior boundary of the middle frontal gyrus 1092, at which the middle frontal gyrus midline 1098a intersects the precentral sulcus 1091, in a manner identical or equivalent to and consistent with that described above with reference to FIG. 3A. FIG. 4B is a bar graph illustrating the change in patient improvement over time. Patients having the posterior-most electrode 1050 spaced from the precentral sulcus 1091 by less than approximately 20 mm, where the spacing is defined in accordance with the aforementioned reference point $rp_1$, are identified by dark bars, and patients having the posterior-most electrode 1050 spaced from the precentral sulcus 1091 by approximately 120 mm or more are identified by light bars. FIG. 4C distinguishes among patients who were strong responders, moderate responders, and non-responders to cortical stimulation therapy, as a function of 1) an as-implanted distance between the most posterior electrode 1050 of the electrode device 1000 and the aforementioned precentral sulcus reference point or location $rp_1$; and 2) a superior-inferior electrode offset or displacement relative to the aforementioned middle frontal gyrus midline 1098a. Strong responders were defined as patients who achieved a reduction in their HDRS score of at least 50% most of the time. Moderate responders were those patients who achieved at least some periods of 50% HDRS reduction, and non-responders did not achieve an HDRS reduction of 50%.

The results depicted in FIGS. 4A-4C indicate that a more significant and/or more favorable therapeutic response occurs when stimulation signals are applied at and/or anterior to a middle frontal gyrus location that equals or exceeds a curvilinear, approximately curvilinear, or approximately linear target minimum distance $d_t$ from the precentral sulcus 1091. Depending upon embodiment details, the target minimum distance $d_t$ can additionally or alternatively be defined relative to the central sulcus 1090 and/or another anatomical structure or landmark. The results further indicate that a more significant therapeutic response occurs when stimulation signals are applied superior or dorsal to the midline or approximate midline 1098a of the middle frontal gyrus 1092.

As indicated in FIG. 4A, when a posterior-most electrode 1050 was positioned approximately 16 mm or closer to the precentral sulcus 1091, patient improvement was minimal or clinically insignificant. A small or very small anterior shift or translation of the most-posterior electrode position (e.g., an anterior shift of the most-posterior electrode by approximately 2-4 mm) resulted in a very substantial patient improvement. The dramatic extent to which patients' HDRS scores improved (i.e., the achievement of clinically significant improvement versus minimal or essentially no improvement), relative to a small or very small difference in the most-posterior electrode position was a surprising and unexpected result to the inventors. For example, it was unexpected that such a substantial improvement would occur for each patient within the subset of patients experiencing noticeable or clinically measurable improvement. This electrode positioning result was further surprising in view of the characteristics of the patient population involved in the clinical trial. In particular, these patients were treatment-resistant patients who had failed, on average, nine prior therapeutic interventions (e.g., drug therapies, and/or electroconvulsive shock therapy (ECT)).

A further significant result was the degree to which clinical responders continued to improve over time, particularly in view of the lack of improvement over time shown by cortical stimulation nonresponders. Such improvement over time can indicate that the applied stimulation signals effectively facilitated beneficial neuroplastic processes or changes (e.g., in neural pathways or circuits involved in processing emotional responses), where such neuroplastic changes may have the potential to transition at least some patients to near-complete, essentially complete, or periodically complete symptomatic remission. A small or very small difference in electrode position can have a significant impact on the likelihood of achieving neuroplastic change.

In one embodiment, $d_t$ can be defined as a minimum distance between a reference point $rp_1$ defined in a manner identical or analogous to or consistent with that described above and a location at which an electrode device or a most-posterior electrode or set of electrodes carried by the electrode device is implanted. Depending upon embodiment details, the reference point $rp_1$ can be defined as 1) the approximate point or location along the posterior wall of the middle frontal gyrus 1092 at which a generally bisecting middle frontal gyrus midline 1098a intersects the precentral sulcus 1091; 2) the most anterior precentral sulcus location that is closest to the midline or approximate midline 1098a of the middle frontal gyrus 1092; or 3) the most anterior location of the precentral sulcus 1091 that abuts the middle frontal gyrus 1092.

In certain embodiments, $d_t$ can be defined to have a terminus that resides at or along a line or an arc that generally bisects the middle frontal gyrus into superior and inferior portions as the line or arc extends in an anterior-posterior direction from the precentral sulcus 1092 (and/or the central sulcus 1090) through the middle frontal gyrus 1092. In other words, $d_t$ can be defined to terminate approximately halfway between the superior frontal sulcus and the inferior frontal sulcus, at a particular distance on or along a line or arc that extends from the precentral sulcus 1091 or the central sulcus 1090 into the middle frontal gyrus 1092. In other embodiments, $d_t$ can be defined to have a terminus that resides at or along a line or an arc that divides a superior portion 1092$s$ of the middle frontal gyrus 1092 into approximately equal halves. In still another embodiment, $d_t$ can have a terminus at the most-anterior portion, segment, curve, apex, or projection of the precentral sulcus 1091 along the superior-inferior extent of the middle frontal gyrus 1092.

In various clinical situations (e.g., treating MDD), the minimum target distance $d_t$ can be at least approximately 15 mm, or at least approximately 18 mm, and more particularly at least approximately 15-35 mm, or at least approximately 20-40 mm or approximately 25-30 mm anterior to the precentral sulcus 1091. The target distance $d_t$ can be at least approximately 25-85 mm, and more particularly at least approximately 40-60 mm (e.g., approximately 50 mm) anterior to the central sulcus 1090. Other suitable values for $d_t$ are described later, with reference to FIGS. 5A-5D. These target distances include locations that are at and/or anterior to the middle one-third of the middle frontal gyrus 1092. These target distances also include locations that are at and/or anterior to the mid-dorsolateral prefrontal region. Preferentially applying stimulation signals to (and/or detecting neuroelectric signals from) neurons that are at, approximately at, and/or more anterior to the foregoing representative $d_t$ values is expected to be more beneficial than targeting neurons that are closer to the precentral sulcus 1091 or the central sulcus 1090.

The foregoing preferential neural targeting (e.g., by way of preferential electrode implantation location and/or preferential stimulation signal delivery) can facilitate an enhanced acute and/or chronic response to a therapy regimen that includes neural stimulation in combination with one or more adjunctive therapies. Representative adjunctive therapies include drug therapy or behavioral therapy (e.g., cognitive behavioral therapy, counseling, and/or biofeedback, for instance, in association with neural monitoring operations) directed toward alleviating or managing neuropsychiatric dysfunction. Moreover, as indicated by results shown in FIG. 4C, preferential neural targeting in accordance with various embodiments of the present disclosure may prepare or "prime" a patient's brain for increased beneficial neuroplasticity over time, such that the patient is or becomes increasingly receptive to one or more additional therapeutic interventions, which can include additional neural stimulation, drug therapy, or behavioral therapy.

Depending upon patient-specific neuroanatomy, the middle frontal gyrus stimulation locations that reside at, approximately at, and/or more anterior to the foregoing representative $d_t$ values generally correspond or can be expected to correspond to one or more Brodmann areas. These areas include Brodmann area 9, Brodmann area 9/8, Brodmann area 46, Brodmann area 9/46, Brodmann area 8, Brodmann area 10, and Brodmann area 6. Additionally or alternatively, the practitioner can monitor patient function at such locations to facilitate the detection, generation, and/or analysis of neural and/or neural correlate signals corresponding to neurons within one or more of Brodmann areas 9, 9/8, 46, 9/46, 8, 10, and 6. Such a monitoring procedure (e.g., involving EEG, ECOG, neural imaging, or thermal signal detection) can be performed in association or conjunction with the application of extrinsic neural stimulation signals, where such stimulation signals can be delivered to cortical, subcortical, deep brain, cerebellar, spinal column, and/or peripheral nerve targets. Moreover, depending upon embodiment details, extrinsic stimulation signals can be applied using intracranial devices (e.g., intracranial cortical surface or deep brain electrodes) or transcranial devices (e.g., TMS or tDCS devices).

In one representative example, an EEG monitoring system or an ECOG electrode can record neuroelectric signals from neural targets that reside at or anterior to a middle frontal gyrus target distance $d_t$, in association with the application of stimulation signals to cortical targets that reside at and/or anterior to the target distance $d_t$. When monitoring and stimulation operations involve identical or adjacent neural targets, monitoring and stimulation operations can occur in a time-multiplexed manner, or monitoring circuitry can perform filtering or electrical signal blanking operations.

In another representative example, an EEG monitoring system or an ECOG electrode can record neuroelectric signals from neural targets that reside at or anterior to a middle frontal gyrus target distance $d_t$, in association with the application of stimulation signals to subcortical or deep brain targets. Representative targets include portions of the cingulate gyrus, thalamic targets (e.g., the intralaminar thalamic nuclei, the reticular thalamic nucleus, the thalamic peduncle, or the hypothalamus), the amygdala, the nucleus basalis, the hippocampus, the hippocampal or parahippocampal formation, and/or other targets.

In another embodiment, the practitioner can apply stimulation signals to a set of neural targets that reside at and/or anterior to a middle frontal gyrus distance $d_t$ (e.g., approximately or at least 20-25 mm anterior to the precentral sulcus 1091), in association or conjunction with detecting neuroelectric signals from other neutral populations. Suitable populations include 1) middle frontal gyrus neural populations that reside posterior to $d_t$; 2) cortical neural populations that reside within other neuroanatomical areas, regions, or structures, such as neurons within portions of the superior frontal gyrus, the inferior frontal gyrus, or neurons within the temporal and/or parietal cortices (e.g., portions of the posterior lateral superior temporal gyrus, the supramarginal gyrus, or the angular gyrus); and/or 3) deep brain neural populations. For instance, cortical surface stimulation (e.g., using an intracranial grid-type electrode device) can be applied to neural areas that correspond or are expected to correspond to one or more of Brodmann areas 9, 9/8, 46, 9/46, 10, 8, and 6, and neuroelectric signals can be simultaneously or periodically detected (e.g., using a deep brain electrode device) at or proximate to one or more deep brain targets and/or other cortical targets such as those indicated above.

FURTHER/ADDITIONAL EMBODIMENT CONSIDERATIONS

Figure 5A:
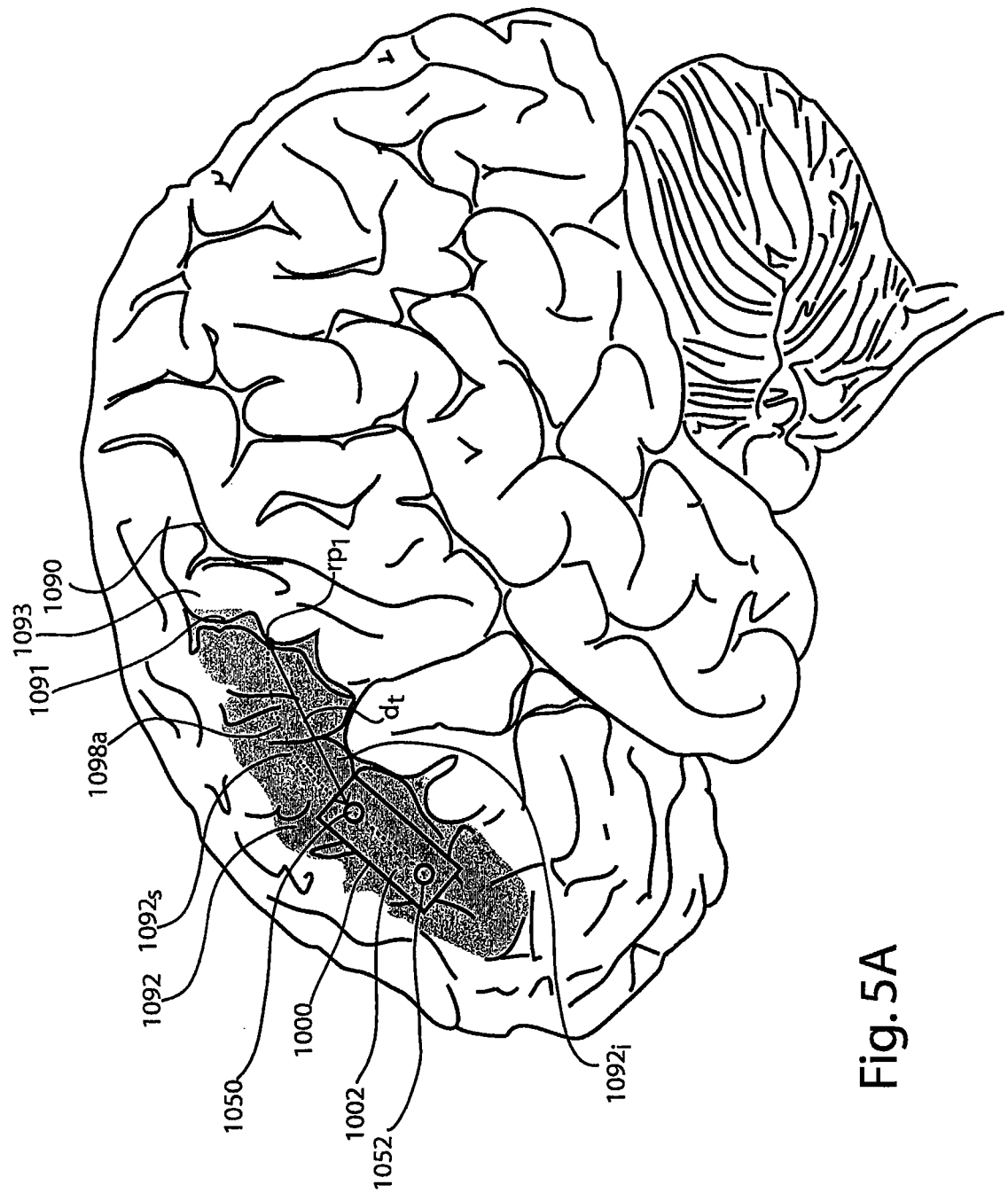
FIG. 5A is a schematic illustration of an electrode device implanted above or upon a patient's middle frontal gyrus in accordance with an embodiment of the disclosure.

FIG. 5A is a schematic illustration of a device 1000 implanted above or upon a patient's middle frontal gyrus 1092 in accordance with a target minimum distance $d_t$ measured from the precentral sulcus 1091 in accordance with an embodiment of the disclosure. In one aspect of this embodiment, the electrode device 1000 device has a structure that is identical or analogous to that described above with reference to FIG. 3A. Depending upon embodiment details, the first and second electrodes 1050, 1052 can be approximately 0.5-4.5 mm (e.g., 3.75 mm) in diameter, and can have a center-to-center spacing of approximately 10-40 mm (e.g., 15 mm, 18 mm, or another suitable spacing). As described above, $d_t$ can be defined as the distance between an edge, center, or approximate center or midpoint of the first electrode 1050 and a particular reference origin along a segment of the precentral sulcus 1091. The reference origin can be identified in the manner described above with reference to FIG. 3A or another suitable technique. For example, the reference origin can be defined in relation to a most anterior projection of the precentral sulcus 1091 that is closest to a midline of the middle frontal gyrus 1092 that generally bisects the middle frontal gyrus into a superior portion 1092s and an inferior portion 1092i.

As discussed previously, $d_t$ can be defined relative to the central sulcus 1090. Accordingly, depending upon patient neuroanatomy, the width of the precentral gyrus 1093 between the central sulcus 1090 and the precentral sulcus 1091 is generally approximately 10-30 mm. Thus, relative to the central sulcus 1090, $d_t$ can be at least approximately 25-85 mm, or approximately 30-70 mm, or approximately 25-65 mm, or approximately 30-60 mm, or approximately 40-60 mm, or approximately 50 mm from a reference point to the posterior edge, center or midpoint of the first electrode 1050, in particular embodiments. Depending upon embodiment details, a central sulcus-based reference point can be defined as the central sulcus location at which a middle frontal gyrus midline or arc 1098a that is extended posteriorly beyond the middle frontal gyrus 1092 intersects the central sulcus 1090. In another embodiment, the reference point can be defined as the most anterior point along a crest or projection of the central sulcus 1090 that falls closest to the midline 1098a or which falls within the superior-inferior span of the middle frontal gyrus 1092. The span can be defined by the superior frontal sulcus and the inferior frontal sulcus, curvilinearly extended to the central sulcus as necessary. The centers of the first electrode 1050 and the second electrode 1052 can be positioned to approximately intersect or reside along, proximate to, or above the middle frontal gyrus midline 1098a. In other embodiments, $d_t$ can be defined relative to a given neuroanatomical structure and the second electrode 1052 or other electrodes, or relative to one or more other structural aspects of the electrode device 1000.

Figure 5B:
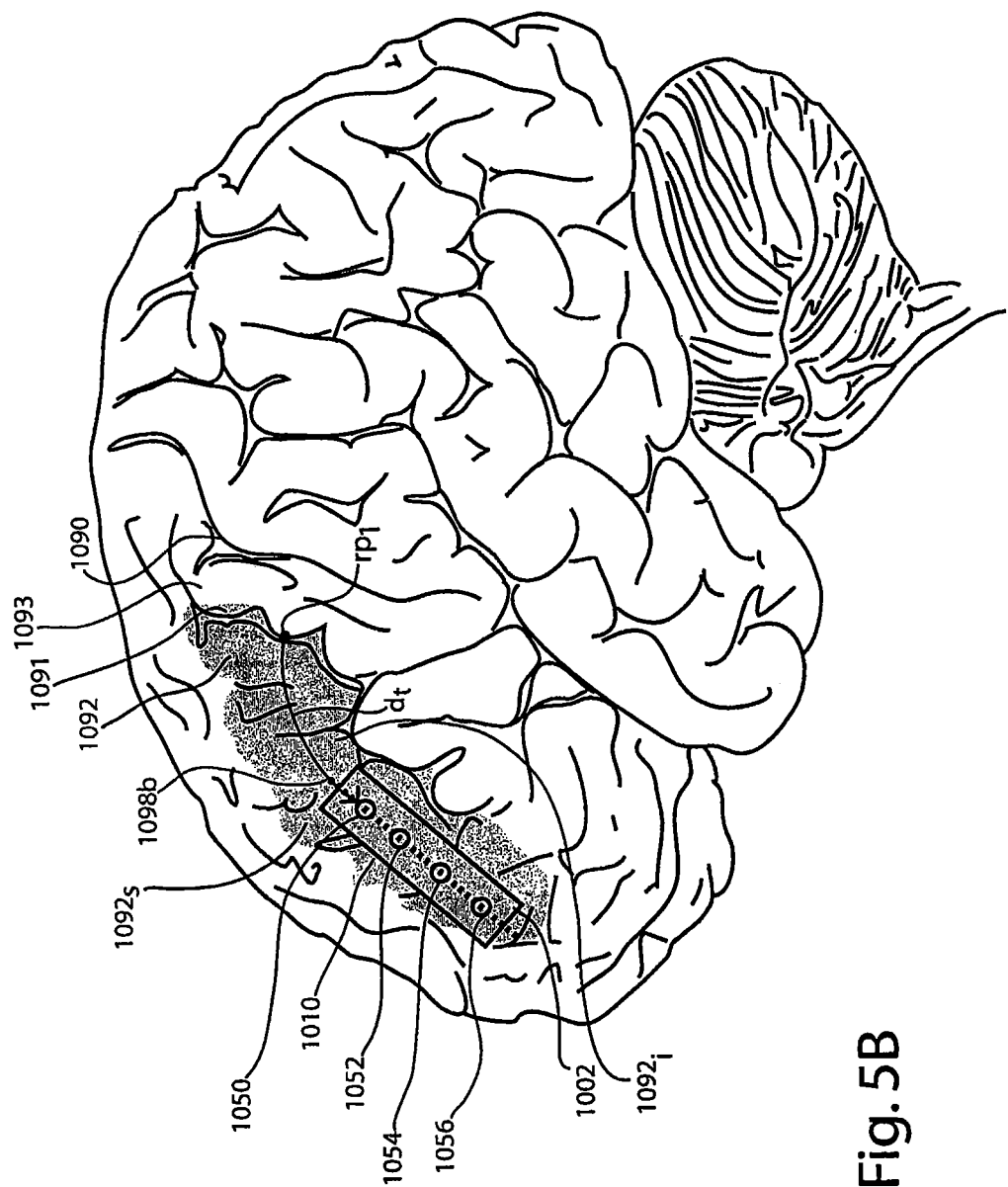
FIG. 5B is a schematic illustration of an electrode device implanted above or upon a patient's middle frontal gyrus in accordance with another embodiment of the disclosure.

FIG. 5B is a schematic illustration of an electrode device 1010 configured in accordance with another embodiment of the disclosure and implanted above or upon the patient's middle frontal gyrus 1092 in accordance with a target minimum distance $d_t$ measured from the precentral sulcus 1091. In this embodiment, the device 1010 includes a support member 1002 that carries a first, a second, and a third electrode 1050, 1052, 1054, and possibly an $n^{th}$ electrode 1056, where n is greater than or equal to 4. The value of $d_t$ can be defined in a manner that is identical or analogous to that described above with reference to FIG. 3A, 3B, or 5A. In several embodiments, the electrode device 1010 can be positioned such that as many electrodes 1050-1056 as possible reside above, along, or proximate to the middle frontal gyrus midline 1098b that generally bisects at least a portion of the middle frontal gyrus 1092 as the midline 1098b extends into or through the middle frontal gyrus 1092 from the precentral sulcus 1091 and/or the central sulcus 1090 in an anterior-posterior direction.

Figure 5C:
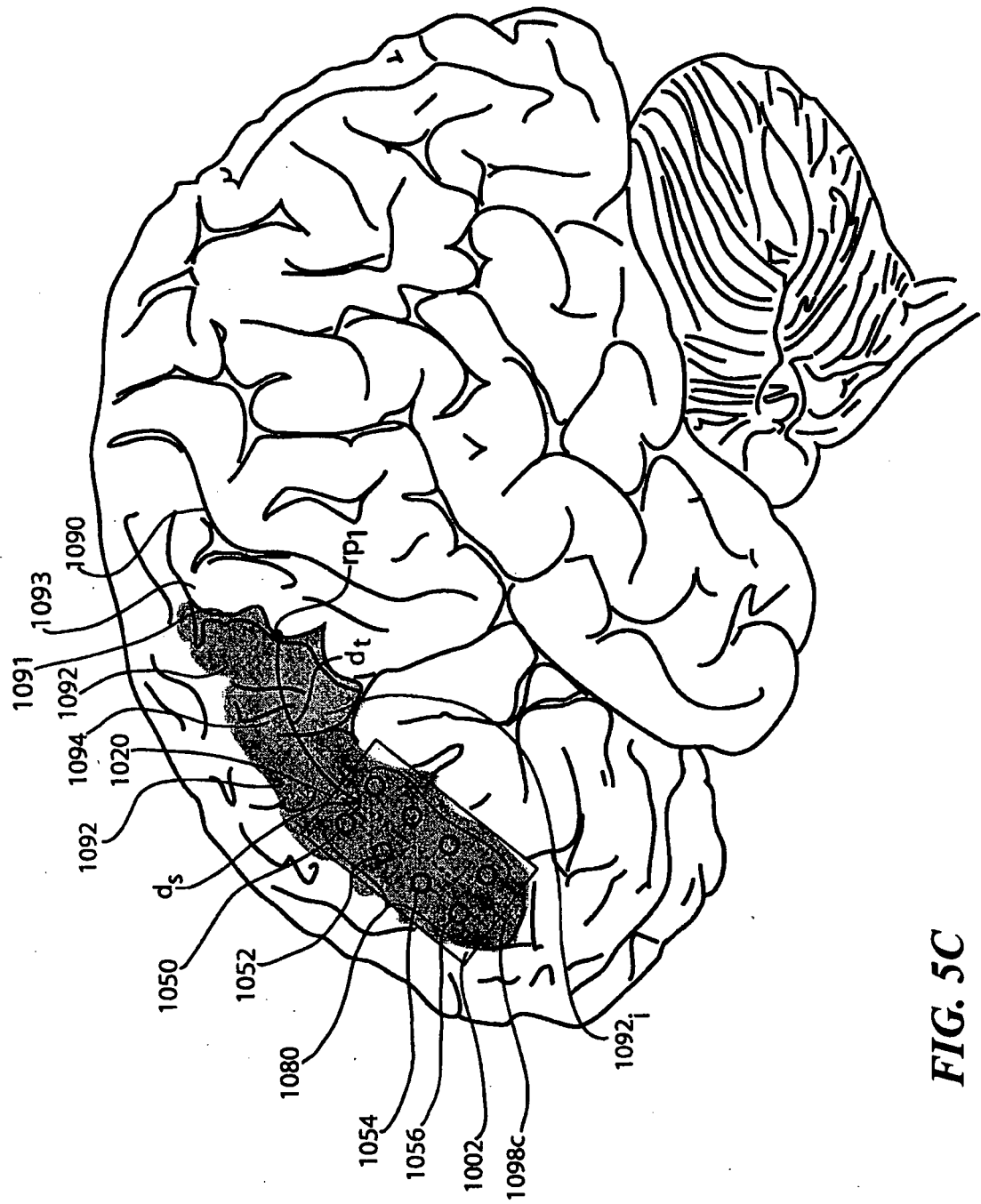
FIG. 5C is a schematic illustration of an electrode device implanted above or upon a patient's middle frontal gyrus in accordance with yet another embodiment of the disclosure.

FIG. 5C is a schematic illustration of an electrode device 1020 configured in accordance with yet another embodiment of the disclosure and implanted above or upon a patient's middle frontal gyrus 1092 with a suitable target distance $d_t$. In one aspect of this embodiment, the electrode device 1020 includes a support member 1002 that carries a first and a second row of electrodes 1080, 1082, where each electrode row 1080, 1082 includes at least a first electrode 1050 and possibly up to an $n^{th}$ electrode 1056. In one embodiment, the value of $d_t$ can be defined as a distance (e.g., approximately 10-40 mm, or approximately 15-30 mm, or approximately 20-25 mm) from a reference point on the precentral sulcus 1091 to a midpoint between the first and second electrode rows 1080, 1082, for instance, midway between the centers or nearest edges of each electrode row's first electrode 1050. Accordingly, one or more electrodes can be positioned more than 35 mm anterior to the reference point. In one embodiment, the electrode device 1020 can be positioned such that each electrode row 1080, 1082 is approximately equidistant from (e.g., parallel to) the middle frontal gyrus midline 1098a, or such that a superior electrode row 1080 and an inferior electrode row 1082 are approximately equidistant from the superior frontal sulcus (not shown) and the inferior frontal sulcus (not shown), respectively.

Referring to FIG. 4B and FIG. 5C together, clinical trial results shown in FIG. 4C indicate that therapeutic efficacy can be enhanced when electrically active or stimulating electrodes are implanted above, upon, or within the middle frontal gyrus 1092 at one or more locations that are superior or dorsal to a midline 1098c that approximately bisects the middle frontal gyrus 1092 into superior and inferior portions 1092s, 1092i. Thus, in certain embodiments, at least some electrodes of the electrode device into (e.g., electrodes in the first row 1080 shown in FIG. 5C) can be implanted at a given distance $d_s$ superior or dorsal to an approximate middle frontal gyrus midline 1098c with respect to an electrode edge or center. Depending upon embodiment details, $d_s$ can be approximately 2-10 mm, or more particularly, approximately 3-7 mm, or approximately 5 mm from the middle frontal gyrus midline 1098c and the inferior or ventral edge of the most posterior electrode 1050, e.g., a most posterior electrode within a superior electrode row 1080. The superiorly-positioned electrodes can be located within the middle frontal gyrus 1092, and/or they can be located within the adjacent superior frontal gyrus, for instance, at an inferior portion of the superior frontal gyrus.

In certain embodiments, an electrode device is implanted such that it can apply stimulation signals using electrodes that are at and/or anterior to $d_t$ as well as at and/or superior to $d_s$. Such electrode positioning can enhance a likelihood of preferentially applying stimulation signals to Brodmann are 9/46. In some embodiments in accordance with the present disclosure, stimulation signals can be initially or preferentially applied to electrodes that reside above or within the superior portion 1092s of the middle frontal gyrus 1092. Sets of electrodes that reside outside of the superior portion 1092s of the middle frontal gyrus 1092 can be selectively activated depending upon their contribution to therapeutic efficacy.

In general, multiple types of electrode devices can be implanted in a patient and configured to apply electromagnetic signals and/or monitor neuroelectric signals. Different electrode devices can have different dimensions, electrode configurations, and/or geometric shapes. In some situations, a pre-surgical planning and/or a surgical implantation protocol can specify one or more target implantation distances $d_t$ at or near which particular electrodes and/or predetermined portions of an electrode device are implanted relative to one or more neuroanatomical landmarks. In addition, a treatment protocol (e.g., a stimulation and/or monitoring protocol) can specify a treatment set or subset of electrodes defined to initially or continually reside within or span a target treatment area or region. Moreover, one or more of the treatment set electrodes can be defined to reside at a target minimum distance $d_t$ from a neuroanatomical landmark (e.g., anterior to the precentral sulcus 1091) and/or a target implantation distance $d_i$.

Figure 5D:
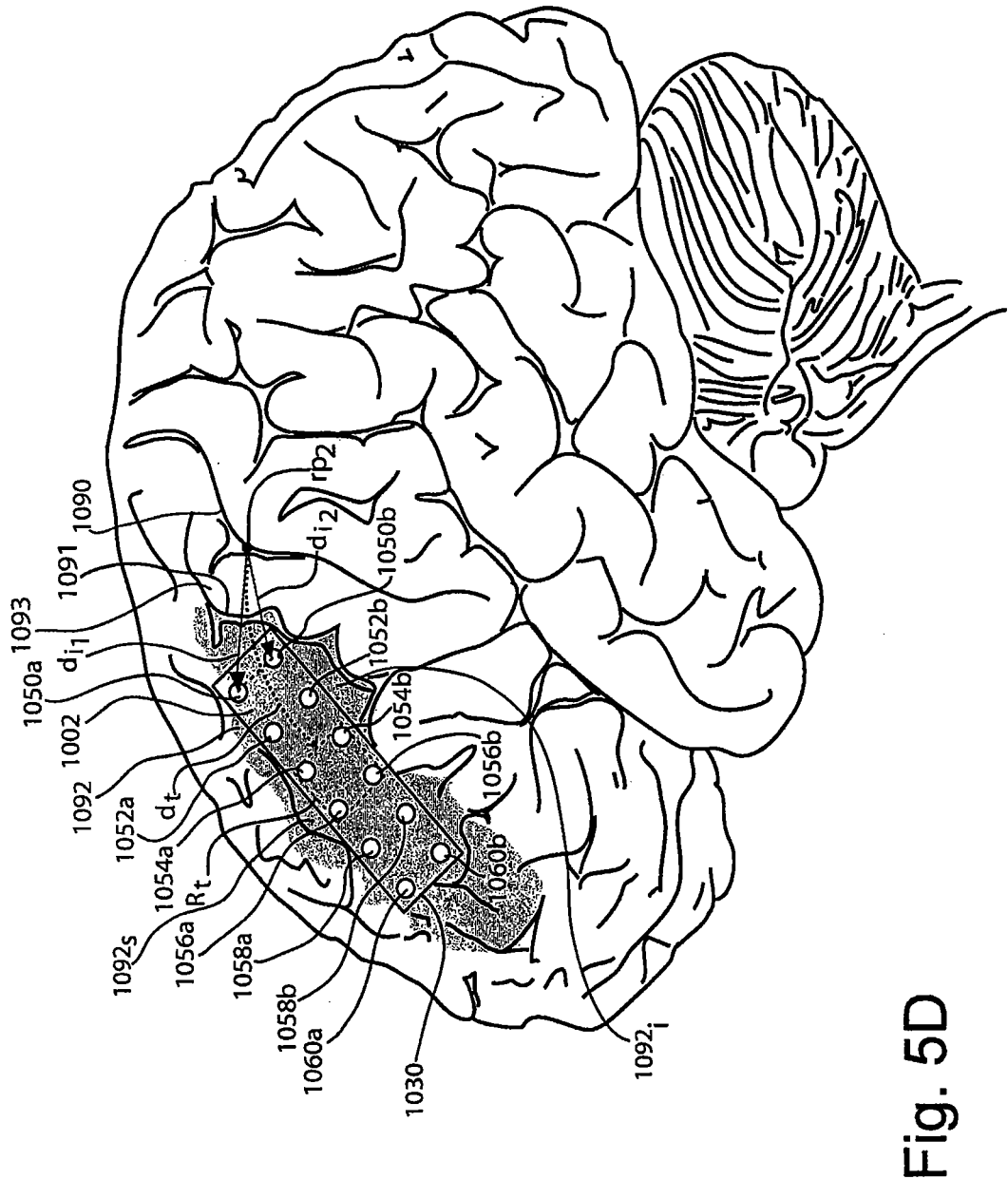
FIG. 5D is a schematic illustration of an embodiment of an electrode device implanted above or upon a patient's middle frontal gyrus in accordance with still another embodiment of the disclosure.

FIG. 5D is a schematic illustration of an embodiment of another electrode device 1030 implanted above or upon a patient's middle frontal gyrus 1092 in accordance with a set of target implantation distances $d_{i1}$, and $d_{i2}$ and a target stimulation and/or monitoring distance $d_t$. The first and second target implantation distances $d_{i1}$, $d_{i2}$ can each correspond to a distance at which a corresponding electrode 1050a, 1050b is positioned relative to an anatomical landmark such as the central sulcus 1090. In another embodiment $d_{i1}$ and $d_{i2}$ can be measured relative to the electrode device 1030, or a portion of the electrode device 1030 such as a posterior support member boundary, midpoint, or corner. In either embodiment, a reference point $rp_2$ upon the central sulcus 1090 (e.g., at a location along the anterior side of the central sulcus 1090) can serve as an origin for the target implantation distances $d_{i1}$, $d_{i2}$. The reference point $rp_2$ can be defined as the most anterior feature, crest, or projection of the central sulcus 1090. By implanting the electrode device 1030 with references to two or more target implantation distances $d_{i1}$, $d_{i2}$, the practitioner can enhance the accuracy with which the electrodes and/or electrode device are positioned. In particular, this technique can improve the accuracy of the angular or rotational orientation of the electrode device 1030.

Once the electrode device 1030 is implanted, certain electrodes may be posterior to the target distance $d_t$. Accordingly, such electrodes may be selectively deactivated to conserve power, and electrodes within a target treatment region $R_t$ can remain active. In one embodiment, the target treatment region $R_t$ can be defined to include particular electrodes 1052a, 1052b, 1054a, 1054b that are at, approximately at, and/or anterior to $d_t$. In other embodiments the target treatment region $R_t$ can be defined to include each electrode that is anterior to $d_t$, or specific electrodes within a given radius of $d_t$, or electrodes positioned within a predetermined anteroposterior distance or range relative to $d_t$, or particular electrodes that are at or anterior to $d_t$ as well as superior or dorsal to a middle frontal gyrus dividing line (e.g., a bisecting midline as described above). In specific embodiments, multiple target treatment regions $R_t$ can be defined, possibly including separately defined target treatment regions $R_t$ for the delivery of stimulation signals and the detection of neuroelectric signals, where separately defined target treatment regions $R_t$ can be spatially distinct or overlapping.

In particular clinical situations, a target treatment region $R_t$ can be a brain area to which stimulation signals are initially applied e.g., for a period of minutes, hours, days, weeks, or months. Depending upon an extent of therapeutic benefit or a symptomatic improvement trend, a target treatment region $R_t$ can remain as originally defined, or adjusted. As a representative example, a target treatment region $R_t$ can be expanded to include additional electrodes. As another representative example, $R_t$ can retain its originally defined shape, size, or area, but can be shifted in an anterior or posterior direction, possibly depending upon particular structural aspects of the associate electrode device and/or the manner in which $d_t$ is defined. A target treatment region can alternatively be consolidated or reduced in size, depending upon therapeutic effect, possibly in view of power consumption. For example, the target treatment region can be reduced during expected sleeping hours, and/or to conserve power in the event that a smaller target treatment region provides sufficient therapeutic efficacy when the patient is awake. As a further approach to conserving power and/or focusing the stimulation signals to have a significant effect, all the active stimulation electrodes implanted within the patient's skull cavity (e.g. all stimulation electrodes actively delivering stimulation signals) are implanted outside the cortical surface of the patient's brain at the patient's middle frontal gyrus 1092, in a particular embodiment. In a particular aspect of this embodiment, all such electrodes can be positioned at least 15 mm anterior (e.g. 15-35 mm anterior) to the precentral sulcus reference point $rp_2$.

The delivery of neural stimulation signals to neural populations using electrode devices implanted in accordance with various embodiments of the present disclosure can result in the application of stimulation signals to neural populations within two or more, or in some embodiments three or more, of Brodmann areas 9, 9/8, 46, 9/46, 8, 10, and/or 6. In one embodiment, an electrode device is implanted such that electrodes that reside approximately at and/or anterior to $d_t$ can apply stimulation signals to both Brodmann area 9 and Brodmann area 8 (e.g., simultaneously, or in an alternating, programmable, or aperiodic manner). In another embodiment, an electrode device is implanted such that electrodes positioned at and/or anterior to $d_t$ can apply stimulation signals to Brodmann areas 9 and 10; or Brodmann area 9 and at least one of Brodmann area 9/8 and Brodmann area 6; or Brodmann areas 9, 10, and 8; or Brodmann areas 9, 46, and one or more of Brodmann areas 9/8, 8, and 10; or Brodmann areas 9 and 9/46, plus at least one of Brodmann areas 9/8, 8, 10, and 46. In particular embodiments, stimulation signals are applied to Brodmann area 8 in combination with the stimulation applied to one of Brodmann areas 6, 9, 9/8, 10, 46 and 9/46. For still further embodiments, stimulation is applied to Brodmann areas 8, 9, and 10, and one of 6 or 9/46. In any of these embodiments, an electrode device can be implanted such that electrodes are also positioned in accordance with a superior electrode offset distance $d_s$, in a manner that facilitates the preferential application of stimulation signals to a superior or dorsal portion of the middle frontal gyrus, and/or inferior portion of the superior frontal gyrus. In a particular aspect of at least some of the foregoing embodiments, all active stimulation electrodes implanted within the patient's skull cavity can be located at the foregoing Brodmann areas.

Some electrode device embodiments can include electrodes 1050, 1052, 1054, 1056 that are arranged, organized, or positioned in a curvilinear organization or along an arc rather than in a linear organization. An arc along which electrodes 1050, 1052, 1054, 1056 are positioned can be predefined such that the electrodes carried by an as-manufactured electrode device will conform or approximate conform to the curvature of a particular portion or section of a neuroanatomical region or structure, such as an expected curvature of the crown of the middle frontal gyrus 1092. As with other electrode device embodiments described herein, electrodes included in such curvilinear configurations can apply stimulation signals to and/or monitor neuroelectric signals within portions of neuroanatomical regions that correspond, generally correspond, or are expected to correspond to one or more of Brodmann areas 6, 8, 9, 9/8, 10, 46, and/or 9/46, or two or three or more of such areas in a manner identical or analogous to that described above.

In certain situations, the application of stimulation signals in accordance with various embodiments of the present disclosure to particular therapeutically relevant portions of two or more of the aforementioned Brodmann areas can synergistically facilitate or enhance therapeutic efficacy. As a representative example, the application of stimulation signals to portions of Brodmann area 8 at a minimum target distance $d_t$ that is at least approximately 15-20 mm anterior to a precentral sulcus reference point $rp_1$ (e.g., as shown in FIG. 5A) can beneficially reduce an extent to which a patient experiences an emotional state corresponding to hopelessness and/or uncertainty. Correspondingly or equivalently, preferentially delivering stimulation signals to neural populations within Brodmann area 8 that reside at least approximately 15 mm or more than approximately 18-20 mm anterior to the reference point $rp_1$ can increase an extent to which a patient feels hopeful about a situation or the future. Additionally, the application of stimulation signals to portions of one or both of Brodmann areas 9/8, 9, and/or 10 at a minimum target distance $d_t$ that is at least approximately 20-35 mm anterior to the precentral sulcus reference point $rp_1$ can enhance the patient's ability to concentrate and/or cognitively assess and process emotional input(s) in a more objective, detached, or emotionally balanced manner. A combination of enhanced hopefulness (or reduced hopelessness), reduced uncertainty, enhanced concentration, and/or improved cognitive objectivity can synergistically alleviate or facilitate the alleviation of (e.g., as a result of neural stimulation by itself, or neural stimulation in combination with an adjunctive therapy) one, two, or more neuropsychiatric disorder symptoms, which can include, for instance, excessive worry, excessive feelings of guilt, overly-critical and/or frequent self-deprecation, and thoughts relating to self-destructive behaviors (e.g., self-mutilation or suicidal thoughts).

Semi-Automated or Automated Implantation/Stimulation Site Targeting Procedures

Particular processes within a pre-surgical planning protocol, a surgical implantation protocol, and/or a treatment protocol can be facilitated through the use of computerized, semi-automated, or automated techniques. In particular, computer-aided imaging data acquisition, normalization, and analysis can facilitate the automated or semi-automated identification, definition, or delineation of an electrode or electrode device implantation site, one or more neuroanatomical regions of interest (e.g., portions of the middle frontal gyrus 1092), and/or one or more subregions of interest in view of desired stimulation and/or monitoring operations. Particular aspects of computerized, semi-automated, and/or automated techniques in accordance with various embodiments of the present disclosure can be facilitated through the use of stereotactic neurosurgical planning and/or intraoperative image guided surgery systems, such as a Medtronic StealthStation® (Medtronic, Inc., Minneapolis, Minn.).

For a particular type of neurologic dysfunction under consideration (e.g., MDD), one or more efficacious or generally efficacious electrode implantation locations or signal delivery and/or monitoring sites or positions can be determined based upon existing clinical data obtained in association with the application of neural stimulation therapy to at least one, and preferably multiple, patients. In a manner identical, analogous, or generally analogous to that shown in FIGS. 4A and 4C, within or outside the context of a clinical trial (e.g., during an investigational trial, or following an investigational trial as a recommended or optional part of a post-trial neurosurgical intervention therapy) particular electrode implantation and/or stimulation signal delivery locations or sites that provide a desired level of therapeutic benefit across a given set of patients can be grouped or pooled. These data can be analyzed to define at least one range, distribution, span, nexus, or set of adequately or significantly efficacious signal delivery sites that are common or approximately common to the particular set of patients under consideration. A distribution of efficacious stimulation sites can be mapped to an electrode device mask or outline having representative electrodes located at particular positions within the mask in a manner that enhances or maximizes a likelihood that the neural stimulation signals applied to most patients via an electrode device corresponding the electrode device mask can be expected to provide adequate or significantly efficacious therapeutic results.

The electrode device mask can be defined, generated, overlaid, mapped, and/or positioned upon a standard brain atlas at a predetermined set of atlas coordinates, positions, or locations that are referenced to a neuroanatomical atlas reference point, such that a neurosurgeon understands with a high degree of certainty and/or precision where an actual electrode device corresponding to or manufactured as an implementation of the electrode device mask should be implanted or positioned within a patient. More particularly, the electrode device mask can be positioned upon a standard brain atlas such that one or more representative electrodes of the electrode device mask are located a target minimum distance $d_t$ away from (e.g., anterior to) at least one neuroanatomical reference point or origin upon the standard brain atlas. Any given neuroanatomical reference point upon the standard brain atlas can be defined or identified in a predetermined or pre-programmed manner. In other embodiments, one or more reference points can be identified on an as-needed basis by a neurosurgeon, or retrieved from memory in the event that the neurosurgeon had identified or defined (e.g., using a mouse or a light pen) such a reference point during a previous surgical planning session. In still further embodiments, one or more reference points can be identified semi-automatically or automatically by program instructions or software based upon a neurosurgeon's input and/or meta-data corresponding to a given patient's imaging data and/or medical history. A set of neuroanatomical reference points can be defined upon the standard brain atlas in a manner identical or analogous to that described above with reference to particular embodiments of the present disclosure. For instance, an atlas-based neuroanatomical reference point $rp_1$ can be defined as a set of $(x, y, z)$ brain atlas spatial coordinates at which a bisecting middle frontal gyrus midline intersects the anterior border of the precentral sulcus. As further described below, an electrode device mask can facilitate enhanced electrode device implantation consistency and/or accuracy from one neurosurgeon to another, which can therefore enhance the consistency and/or efficacy of therapeutic results.

Figure 6:
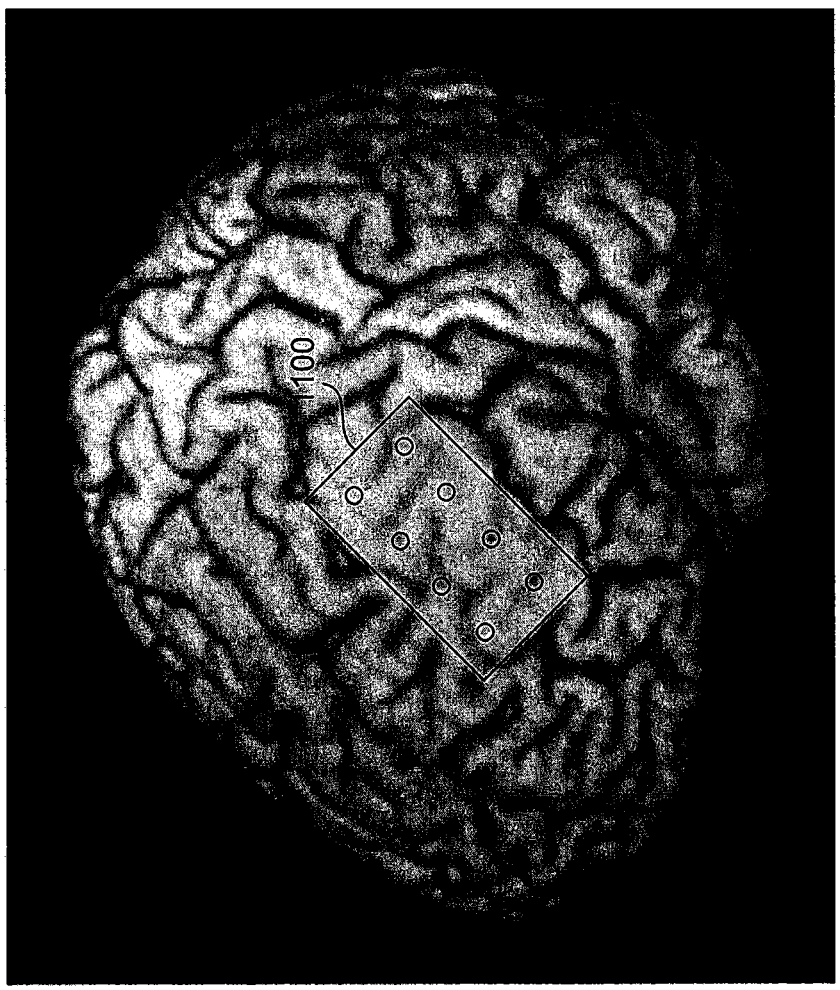
FIG. 6 is an illustration of a representative electrode mask positioned upon a standard brain atlas in accordance with an embodiment of the disclosure.

FIG. 6 is an illustration of a representative electrode device mask 1100 positioned upon a standard brain atlas such as a Talairach or Montreal Neurological Institute (MNI) brain atlas in accordance with an embodiment of the disclosure. Given that a brain atlas is essentially a digital data file, the electrode device mask 1100 itself can correspondingly be a digital data file. As such, the file can include 1) a set of brain atlas coordinates corresponding to each representative electrode (e.g., an electrode center point) defined for the electrode device mask 1100, and possibly 2) a set of brain atlas coordinates and optionally one or more corresponding textual identifiers, for at least one neuroanatomical atlas reference point to which a set of representative electrodes are positionally referenced. Through a semi-automated or automated procedure such as that described hereafter with reference to FIG. 7A, an electrode device mask 1100 can be defined or generated, and mathematically mapped or warped onto an individual patient's structural imaging data (e.g., any given patient's structural MRI scan), thereby specifically tailoring an electrode device's implantation location, and automatically defining, establishing, or adjusting a target minimum distance $d_t$, in accordance with individual patient neuroanatomy.

Figure 7A:
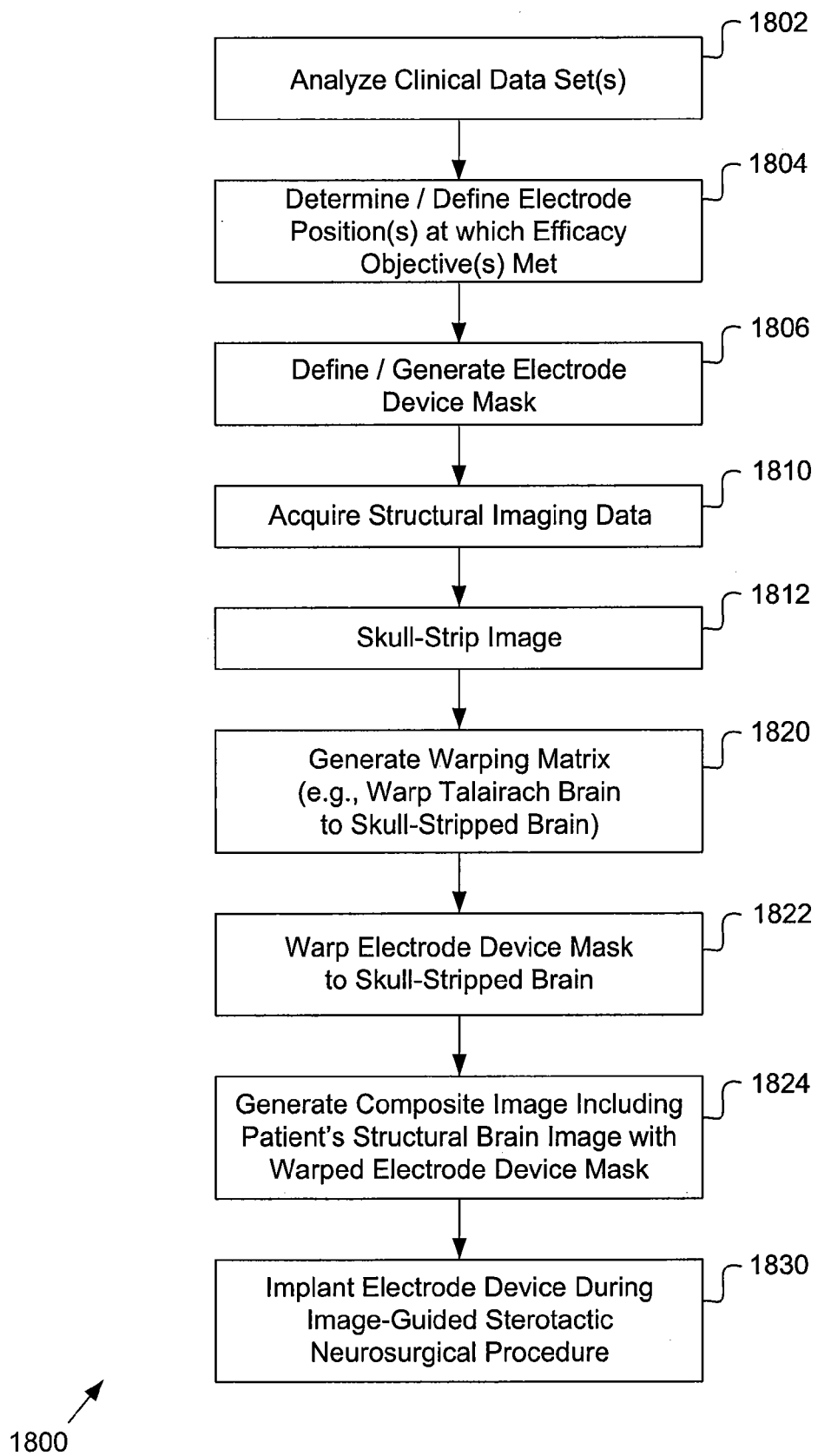
FIG. 7A is a flow diagram illustrating a representative electrode device implantation targeting process in accordance with an embodiment of the disclosure.

FIG. 7A is a flow diagram illustrating a representative electrode device implantation targeting process 1800 in accordance with an embodiment of the disclosure. A first process portion 1802 includes data analysis operations in which at least one clinical data set corresponding to the application of stimulation signals to treat neuropsychiatric and/or neurocognitive dysfunction is analyzed or evaluated, for instance, in a manner that is identical, analogous, or generally analogous to that indicated by FIGS. 4A-4C. This information can be received from a variety of sources, including a practitioner, or a database or other storage medium. A second process portion 1804 includes determining or defining one or more relevant electrode device positions or stimulation signal application locations in accordance with which particular electrodes satisfied a set of efficacy objectives. In one embodiment, an efficacy objective can be a given minimum measured level of improvement in a patient state, condition, or symptom at or within a specified time (e.g., at least a 25% improvement within 6 to 8 weeks, and/or at least a 40% improvement within 12 weeks). Alternatively, an efficacy objective can be a minimum acceptable average improvement when multiple patient evaluation times or intervals are considered (e.g., a sustained average improvement of 50% across clinical patient evaluations performed at or beyond 16 weeks). In a third process portion 1806, electrode mask definition operations are performed in which at least one representative electrode that meets or exceeds a given efficacy objective is defined, generated, and/or positioned upon a brain atlas at set of brain atlas coordinates corresponding to a neuroanatomical atlas reference point.

One or more aspects of the first, second, and/or third process portions 1802, 1804, 1806 described above can be performed manually, semi-automatically, or automatically. For instance, in one representative embodiment a clinical data set can be generated, maintained, and stored upon a computer readable medium such as a memory or hard disk drive. For each patient under consideration, the clinical data set can specify a patient identifier, one or more links to patient imaging data files (e.g., a stored MRI image and/or a stored CT scan), and at least one set of clinical efficacy data for the patient. At scheduled patient evaluation times, clinical efficacy data can be entered (e.g., manually) and stored. A set of clinical efficacy objectives (e.g., minimum or threshold improvement level(s) vs. time) can also be defined and stored. The implanted positions or locations of active electrodes or stimulation sites can be manually, semi-automatically, and/or automatically determined relative to a given neuroanatomical reference point by way of clinician or neurosurgeon identification or definition of the neuroanatomical reference point, followed by an analysis of a patient's imaging data (e.g., measurements made using the patient's CT scan fused with the patient's MRI scan). One or more numerical analyses (which can include a statistical analysis) can be performed (e.g., by software) to characterize clinical efficacy versus stimulation signal application location, and the results of such analyses can be stored on an individual patient and/or a patient group basis. One or more graphs or charts showing clinical results versus active electrode position(s) can be generated and presented to a clinician, a statistician, and/or a neurosurgeon to facilitate the identification of particular active electrode locations as representative electrodes for an electrode device mask definition. In one embodiment, a set of representative electrodes a corresponding electrode device mask can additionally or alternatively be defined or determined automatically.

A fourth process portion 1810 includes structural imaging data acquisition operations, which can include the pre-surgical acquisition of an MRI scan such as a high resolution T1-weighted anatomic scan of a patient's head, including the patient's brain. In a fifth process portion 1812, conventional skull-strip operations are performed, through which skull-related data within the acquired MRI dataset are removed to generate an imaging dataset referred to hereafter as the skull-stripped patient brain. In general, skull-strip operations may not be required; however, in certain embodiments (e.g., depending upon imaging system and/or image processing software capabilities), skull-strip operations can improve the accuracy of subsequent numerical transformations or operations. A sixth process portion 1820 includes atlas warping operations that involve warping a standard brain atlas (e.g., a Talairach atlas) to the skull-stripped patient brain to generate a warping matrix (e.g., a matrix of scaling factors), in a manner understood by one of ordinary skill in the art. The warping matrix transforms a set of standard brain atlas spatial coordinates to a set of patient-specific stereotactic spatial coordinates. In certain embodiments, the skull-stripped patient brain can be mapped to a standard brain atlas, which results in the generation of a transformation or normalization matrix that is the inverse of the aforementioned warping matrix (i.e., the transformation matrix itself is a version of the warping matrix, namely, its inverse). Particular aspects of processes described herein can be performed based upon the skull-stripped brain and/or the atlas brain, and spatial coordinate conversions between patient-specific coordinates and brain atlas coordinates can be performed using a given matrix or its inverse as appropriate.

A seventh process portion 1822 includes mask warping operations through which an electrode device mask 1100 such as the mask shown in FIG. 6 is warped, mapped, or scaled in accordance the aforementioned warping matrix to generate a warped electrode device mask. The mask warping operations transform a set of spatial electrode device mask position and/or orientation coordinates defined for the standard brain atlas to patient-specific stereotactic spatial position and/or orientation coordinates. As a result, one or more target distances $d_t$, electrode displacement distances $d_s$, and relative representative electrode orientations defined upon or with respect to the standard brain atlas can be appropriately adapted or mapped to the specific or individualized neuroanatomy of the patient's brain. As a result of mask warping operations, the dimensions of a warped electrode device mask may differ from those of the corresponding atlas-based electrode device mask 1100 by an amount that exceeds an allowable or acceptable limit (e.g., a size or surface area change exceeding approximately 5-15%, or approximately 10%). In certain embodiments, if mask warping operations give rise to a dimensional change that exceeds an allowable limit, a neurosurgeon can subsequently manually or semi-automatically adjust (e.g., with respect to a neuroanatomical reference point and a target distance $d_t$) one or more portions of the warped electrode device mask to accommodate or more appropriately target or overlay particular patient-specific neuroanatomical structures of interest in view of the as-manufactured dimensions of an actual electrode device to which the warped electrode device mask corresponds. For instance, a neurosurgeon could lengthen, shorten, narrow, or widen portions of a warped electrode device mask to increase the likelihood that a corresponding implanted electrode device appropriately targets 1) neural populations anterior to an intended target distance $d_i$; 2) an intended set of Brodmann areas; and/or 3) an intended portion of a neuroanatomical region such as the middle-third or the anterior two-thirds of the middle frontal gyrus 1092 or the superior portions thereof. Adjustment of warped electrode device mask dimensions can occur in association with mask warping operations and/or the following composite image generation operations.

An eighth process portion 1824 includes a set of composite image generation operations that in turn include adding the warped electrode device mask to or combining or merging the warped electrode device mask with the originally acquired structural imaging data, such that a set of composite imaging data includes the skull-stripped brain, the skull-related imaging data that was previously stripped, and the warped electrode device mask. A ninth process portion 1830 includes a neurosurgical process (e.g., an image guided stereotactical neurosurgery process) that involves using the composite imaging data to implant an electrode device above or upon the brain of the patient from whom the structural imaging data was acquired in association with the fourth process portion 1810. The composite imaging data facilitates enhanced spatio-topographic accuracy and/or precision during an image guided patient-specific surgical implantation procedure in which an electrode device corresponding to the electrode device mask 1100 is implanted in the patient with respect to one or more electrode implantation distances and/or electrode device orientations that are expected to be relevant for enhancing therapeutic efficacy.

In addition or as an alternative to the foregoing process, patient-specific imaging data can be volumetrically normalized, transformed, warped, or mapped onto a standard brain atlas (e.g., a Talairach, a Montreal Neurologic Institute (MNI), and/or other brain atlas) on an image fused basis. An image fusion can involve co-registering multiple sets of imaging data across imaging modalities (e.g., using MRI, DTI, and fMRI images for a patient) to generate a fused image, which can be normalized in accordance with a given brain atlas. Normalization relative to a given brain atlas can facilitate the automated, semi-automated, and/or manual identification or delineation of particular neuroanatomical structures and/or landmarks (e.g., the superior frontal gyrus, the middle frontal gyrus 1092, the precentral sulcus 1091, the central sulcus 1090, and/or other brain structures), typically in association with one or more image processing procedures (e.g., feature extraction, the application of deformation or warping matrices, finite-element analysis, or statistical analysis).

In one embodiment, a pre-surgical planning station includes a computer system and/or computer network upon which image analysis, transformation, processing and/or manipulation software resides and executes. The pre-surgical planning station includes a medical imaging graphical user interface (GUI) that selectively displays portions of normalized images upon one or more display devices (e.g., a computer monitor). The medical imaging GUI typically includes a set of image analysis tools and drawing or selection tools that are responsive to input devices such as a mouse, a trackball, a drawing tablet, or the like.

Following or as part of an image normalization procedure, the image analysis software can automatically or semi-automatically identify particular brain regions or structures, and delineate or outline particular structures in response to neurosurgeon input as part of a predetermined image processing script. In one embodiment, the image analysis software can automatically or semi-automatically (e.g., in response to a neurosurgeon's selection from a brain structure menu) generate or display (expected) borders or outlines corresponding to particular neuroanatomical structures of interest, such as the middle frontal gyrus 1092. The shape of a given structure mask can be computationally determined on a dynamic basis, or pre-determined/pre-generated based upon one or more previous neuroanatomical structure identification processes. A neurosurgeon can shift or adjust the boundaries of a pre-generated or automatically generated mask based upon patient-specific neuroanatomic features. Alternatively, a neurosurgeon can manually outline or mask one or more neuroanatomical structures of interest in the event that a pre-generated or automatically generated mask is undesired or unavailable.

The image analysis and transformation software can subsequently warp the masked, normalized imaging data corresponding to the patient's brain back to the original or patient-source (i.e., non-atlas) brain volume in accordance with a set of warping parameters, after which the image analysis and transformation software can warp the particular structural mask(s) of interest (e.g., a mask, border, or outline) to the original brain volume using this same set of warping parameters. The structure mask, as represented in the original brain volume, indicates an anatomical target region or zone to which an electrode or electrode device implantation procedure is directed.

After a structure mask has been warped onto an original brain volume, the image analysis and manipulation software facilitates the definition of one or more subregions within the structure mask in response to neurosurgeon input (e.g., received from a mouse used to define substructural boundaries within the structure mask). In a representative example, a neurosurgeon can graphically delineate or divide a middle frontal gyrus mask displayed upon the original patient brain volume into three subregions. In another representative example, image processing software can automatically or semi-automatically facilitate the definition and display such subregions based upon a measure of structural mask area or dimensions. Each middle frontal gyrus subregion can have an identical, similar, or different area or spatial extent, depending upon patient neuroanatomy a given type of neurologic function or dysfunction under consideration. In a manner identical or analogous to that described above, in certain embodiments, in the event that a warping process changes a dimension of a structure mask and/or an electrode device mask by more than an allowable or tolerable limit (e.g., approximately 5-10%), a neurosurgeon can adjust one or more portions of the mask(s) to accommodate or more appropriately target, define, overlay, or fit portions of or locations upon particular patient-specific neuroanatomical structures under consideration.

Figure 7B:
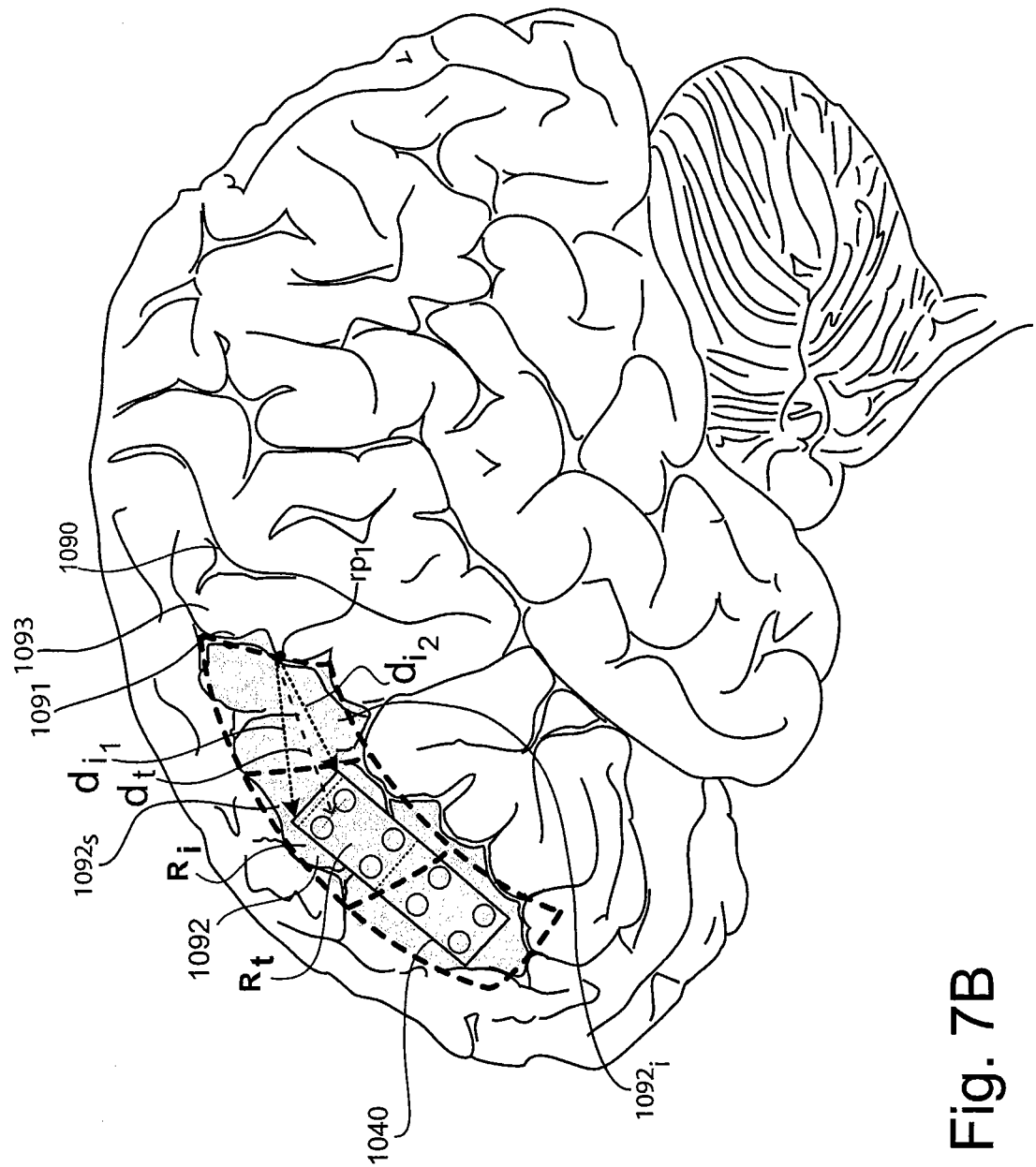
FIG. 7B is a schematic illustration of an electrode device implanted above or upon a patient's middle frontal gyrus in accordance with yet another embodiment of the disclosure.

Referring now to FIG. 7B, the neurosurgeon and/or the image analysis and manipulation software can identify or define a particular subregion, such as the middle third of the middle frontal gyrus 1092, to be a target implantation region $R_i$ at, above, into, within, through and/or below which an electrode device can be implanted. The image analysis and manipulation software can subsequently generate a set of surgical targeting images (e.g., axial, coronal, and sagittal rendered 3D images) to facilitate implantation procedures, during which the neurosurgeon implants an electrode device relative to the target implantation region $R_i$ in view of one or more predetermined target implantation distances $d_{i1}$, $d_{i2}$ and/or a target stimulation and/or monitoring distance $d_t$.

Following the implantation of an electrode device, a post-operative CT image volume can be generated, and registered to or fused with the pre-surgical MRI image volume to identify the brain locations at or above which particular electrodes reside. Specific electrodes and their positions within the target implantation region $R_i$ can be identified, which can facilitate the confirmation of one or more as-implanted distances between a set of electrodes and one or more target distances $d_t$, and/or the confirmation, refinement, or definition of a target treatment region $R_t$ and a corresponding treatment set of electrodes.

Figure 7C:
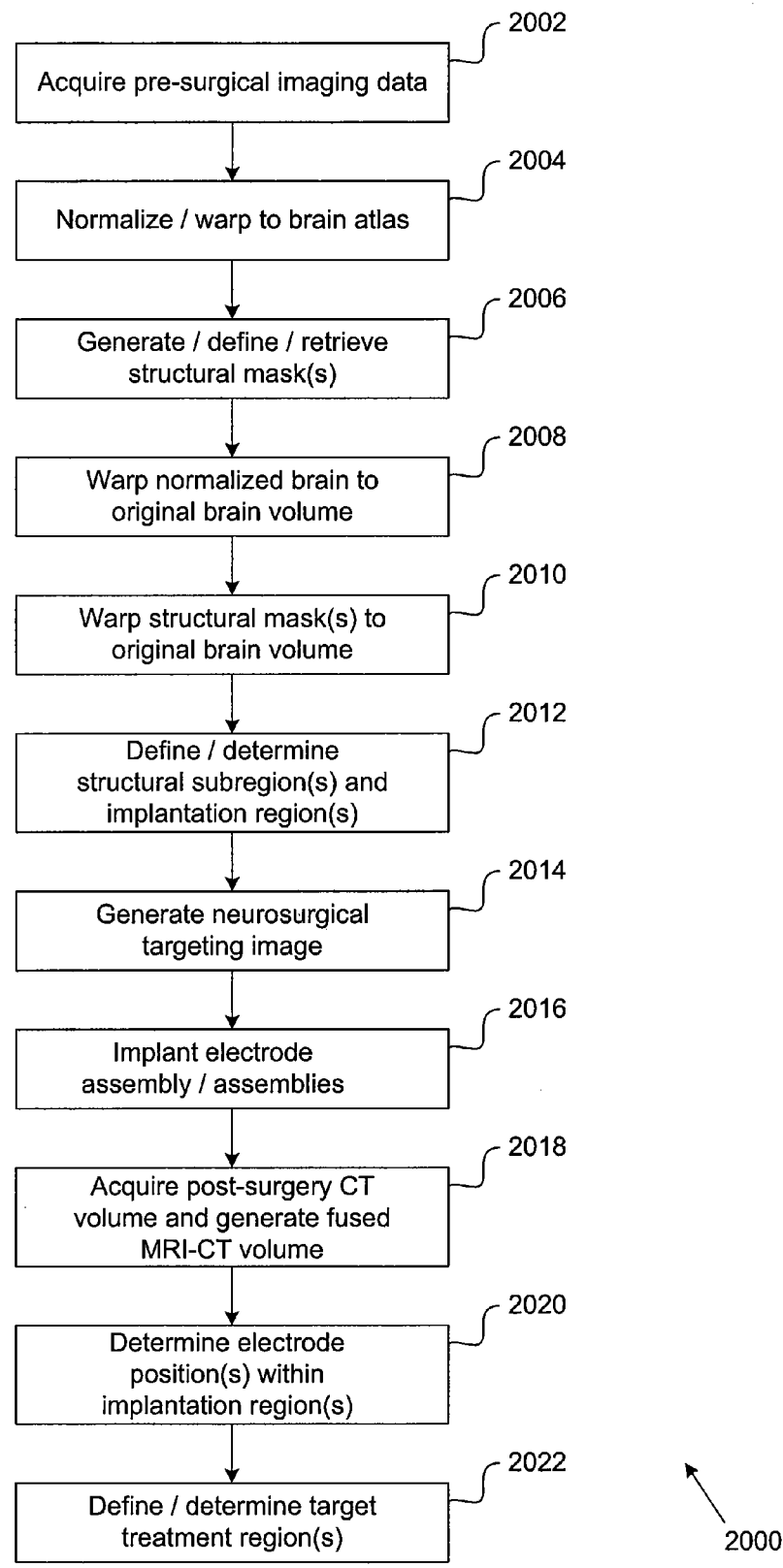
FIG. 7C is a flow diagram corresponding to representative pre-surgical planning, electrode device implantation, and pre-stimulation planning processes according to an embodiment of the disclosure.

FIG. 7C is a flow diagram corresponding to representative pre-surgical planning, electrode device implantation, and pre-stimulation planning processes 2000 according to an embodiment of the disclosure. A first process portion 2002 includes acquiring pre-surgical of MRI imaging data, such as a high resolution T1-weighted anatomic scan of a patient's head, including the entire brain. A second process portion 2004 includes image processing operations to skull-strip the imaging data volume, and warp the patient's brain volume into Talairach space. The second process portion 2004 can be performed using a software package such as AFNI (Analysis of Functional Neuroimages, available through the NIMH in Bethesda, Md.) or FSL (available through the Analysis Group FMRIB, Oxford, UK).

A third process portion 2006 can include generating or loading a structural mask corresponding to the middle frontal gyrus 1092 onto the Talairach-warped brain surface. A fourth process portion 2008 can include warping the Talairach brain volume back to the original brain volume in accordance with a set of warping parameters, and a fifth process portion 2010 can include warping the middle frontal gyrus mask to the original brain volume using this same set of warping parameters to define an anatomical target corresponding to an implantation procedure. A sixth process portion 2012 can include displaying the relevant portions and/or views of the brain and the middle frontal gyrus anatomical target, and defining and graphically indicating a middle third or approximate middle third of the middle frontal gyrus 1092 as a target electrode device implantation region $R_i$. A seventh process portion 2014 can include generating MRI targeting images to assist neurosurgical electrode device implantation procedures, where such MRI targeting images can include axial, coronal, and sagittal rendered 3D imaging data. An eighth process portion 2016 can include implanting an electrode device relative to the actual, estimated, or expected boundaries of the target implantation region $R_i$, in accordance with a set of target implantation distances $d_{i1}$, $d_{i2}$ and/or a target stimulation and/or monitoring distance $d_t$.

A ninth process portion 2018 can optionally include acquiring a post-surgery CT image volume, and registering the post-surgery CT image volume to the pre-surgery MRI volume to generate a fused MRI-CT image volume. A tenth process portion 2020 can include displaying and/or analyzing the fused MRI-CT volume to confirm or determine one or more electrode positions within the implantation region $R_i$, and an eleventh process portion 2022 can include confirming or defining a target treatment region $R_t$ and a corresponding set of treatment electrodes.

One or more portions of pre-surgical planning, electrode device implantation, and pre-stimulation planning processes such as those described herein can facilitate the implantation of an electrode device at a neuroanatomical location (e.g., at or anterior to a target distance from an anatomical reference point such as a location upon the precentral sulcus 1091) within the middle third of the middle frontal gyrus 1092) expected or clinically demonstrated to provide enhanced therapeutic efficacy for a type of neurologic dysfunction or clinical condition under consideration (e.g., MDD).

As previously indicated, one or more Graphical User Interfaces (GUIs) can be generated by a stand-alone or networked computer or computer system and displayed (e.g., to a neurosurgeon) to facilitate the analysis, evaluation, and/or definition of or relationship between at least some of 1) patient and/or atlas based neural structures, features, and/or reference points; 2) actual and/or representative electrode positions; 3) target distances for stimulation signal application; 4) clinical results; and 5) electrode device masks.

Figure 7D:
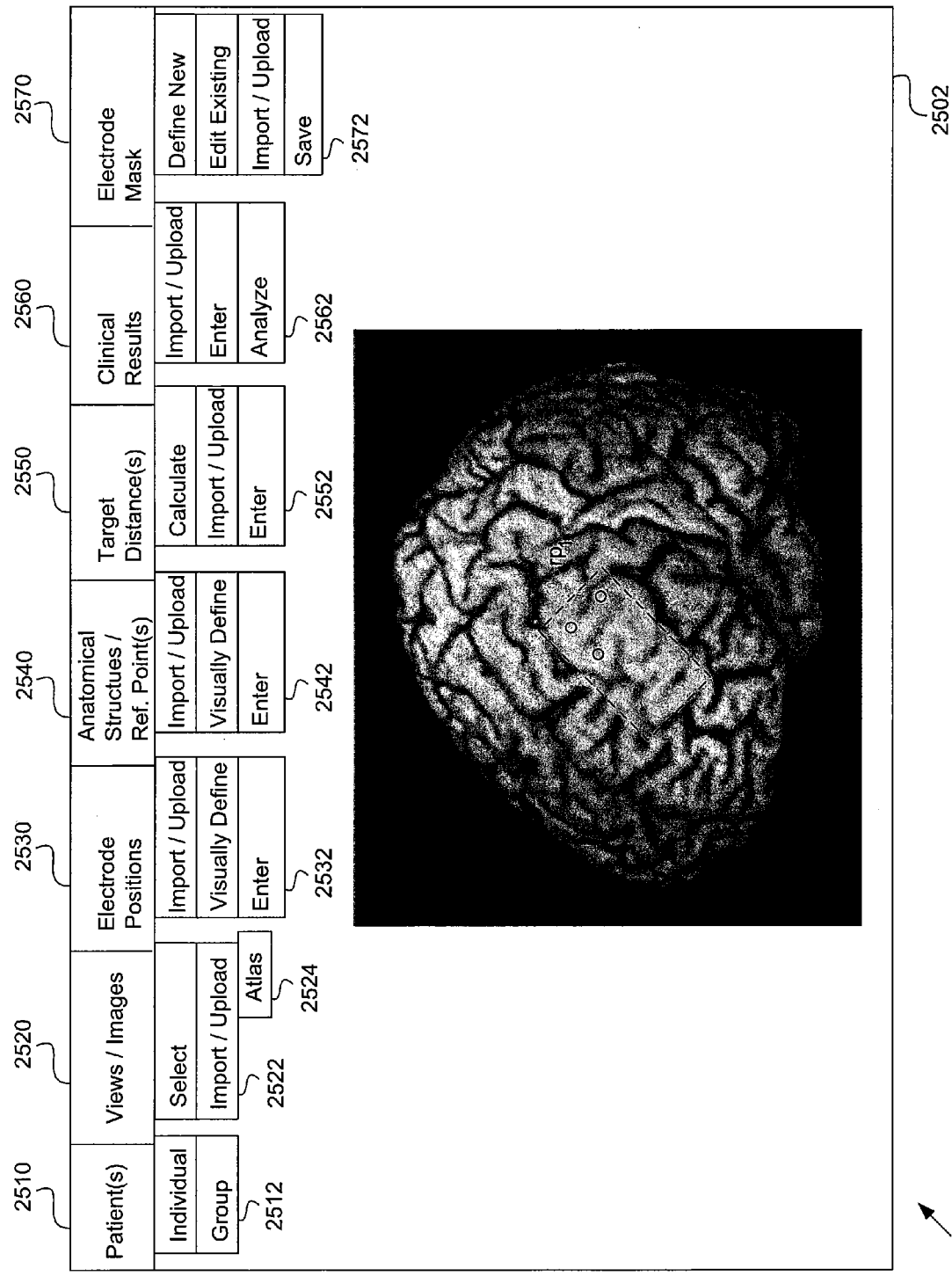
FIG. 7D illustrates a representative graphical user interface in accordance with an embodiment of the disclosure.

FIG. 7D is a schematic illustration of a representative GUI 2500 in accordance with a particular embodiment of the disclosure. In one aspect of this embodiment, the GUI 2500 includes at least one graphical window 2502 that can be visually displayed upon a display device such as a computer monitor. The GUI 2500 further includes a set of selectable (e.g., by way of a pointing device such as a mouse) menus and menu identifiers, which depending upon embodiment details can include at least some of a patient selection menu 2510, an image selection menu 2520, an electrode position menu 2530, an anatomical structure/reference point menu 2540, a target distance menu 2550, a clinical results menu 2560, and an electrode device mask menu 2570.

One or more of the foregoing menus can include at least one submenu, where a given submenu includes a set of selectable identifiers that categorically relate to its parent menu. For instance, the patient selection menu 2510 can include a submenu 2512 having identifiers that facilitate the selection or specification of an individual patient mode or a patient group mode. Similarly, the image selection menu 2520 can include a submenu 2522 having identifiers that facilitate the selection of particular patient-specific images and/or a brain atlas image. Analogously, an electrode position submenu 2532 can include identifiers that, when selected, facilitate the import, definition, or entry of one or more electrode positions upon a displayed brain image. An anatomical structures/reference points submenu 2542 can include identifiers that when selected facilitate the import, definition, or entry of anatomical structures (e.g., the middle frontal gyrus) and/or a neuroanatomical reference point (e.g., a particular point on the precentral sulcus). A target distance submenu 2552 can include identifiers that facilitate the calculation, import, or entry of one or more target distances between a set of neuroanatomical reference points and one or more brain locations, such as a location at which an actual or representative electrode is defined to reside.

A clinical results submenu 2562 can include identifiers that facilitate the import, upload, or entry of clinical data, and the analysis of such data. Clinical data analysis operations can be performed by program instructions (e.g., directed to performing statistical analysis operations, and possibly the generation of graphs, charts, tables, or the like that can visually convey relationships within or between results to a viewer). An electrode device mask submenu 2572 can include identifiers that facilitate electrode device mask definition, modification, import/upload, and storage.

Depending upon embodiment details, a GUI 2500 in accordance with the present disclosure can generate and display one or multiple windows 2502 to a user, where such display can occur on one or multiple display devices in a local or networked manner. The GUI 2500 can respond to the selection and/or manipulation of information displayed within a GUI window 2502 in response to user input received by way of one or more input devices such as a keyboard, a mouse, a trackball, a light pen, a tablet-based pen, and/or other device. In some embodiments, in response to the selection of particular menu or submenu selections, the GUI 2500 can invoke and/or exchange information with one or more software library functions and/or stand-alone software programs (e.g., a spreadsheet or statistical analysis program).

Aspects of Stimulation Procedures

A stimulation procedure directed toward the application of extrinsic stimulation signals to treat neuropsychiatric dysfunction can include one or more time periods in which each electrode of a given electrode device is electrically active (e.g. by delivering stimulation signals and/or monitoring neuroelectric signals (e.g., ECoG)). Additionally or alternatively, a stimulation procedure can include one or more time periods in which particular electrode subsets carried by a given electrode device are electrically active. The activation of each electrode and/or one or more electrode subsets can depend upon the type of neurologic dysfunction under consideration and/or the patient's clinical response, imaging response, and/or electrophysiologically measured (e.g., ECOG or evoked potential) response to the applied stimulation signals.

As a representative example, in an embodiment involving the electrode device 1010 described above with reference to FIG. 5B, an initially active electrode subset can include the first, second, and third electrodes 1050, 1052, 1054. Depending upon the nature and/or extent of a patient's response to the extrinsic stimulation signals (for instance, the presence or absence of a noticeable or favorable acute response, and/or the presence or absence of a beneficial or adverse response that arises over the course of a number of weeks (e.g., 2-12 weeks), additional increasingly anterior electrodes 1056 can be activated at one or more times. Moreover, one or more most-posterior electrodes 1050, 1052 can be deactivated at one or more times, and/or stimulation signals applied to such more-posterior electrodes 1050, 1052 at a reduced intensity or level in the event that clinical, imaging, and/or electrophysiologic data indicates that such electrodes 1050, 1052 provide relatively less or little contribution to therapeutic efficacy.

In addition to the foregoing, in an embodiment involving an electrode device such as any of the electrode devices 1020, 1030, 1040 shown in FIGS. 5C, 5D, and 5E, respectively, any given electrode subset that is active at one or more times can include electrodes within one or both electrode rows 1080, 1082. In certain situations, an initial set or subset of electrodes carried by an electrode device can be used to initially apply stimulation signals. Depending upon embodiment details, the initial set of electrodes can include some or all of the electrodes carried by the electrode device. for example, the initial set of electrode can include each electrode at or anterior to $d_t$, or each electrode that is at or anterior to $d_t$ as well as positioned along a superior (or inferior) electrode row. In other embodiments, this set can include the most-posterior k electrodes that are positioned at or anterior to $d_t$. After a first time period during which the patient experiences a favorable therapeutic response, particular electrodes (e.g., one or more most-posterior electrodes) within the initial set of electrodes can be activated at a reduced signal intensity, level, or duration, or deactivated during a second time period, and the patient monitored to determine whether a sufficiently high or adequate level of therapeutic benefit is present. Such a stimulation procedure can successively, over time, determine a minimum number of active electrodes that are useful for achieving or maintaining therapeutic efficacy. In the event that therapeutic efficacy changes or degrades over time following a generally stable period of therapeutic benefit, the foregoing stimulation procedure can be repeated, or additional electrodes can be successively (re)activated, until a sufficient or desired level of therapeutic benefit occurs. For example, efficacy may change after 6 to 12 months, possibly due to an event in the patient's life that impacts his/her neuropsychiatric or neuropsychologic stability, and the foregoing procedure can adjust the stimulates to reflect this change.

Referring again to FIGS. 1A and 1B, in various embodiments, a stimulation system can include elements that are configured to sense, measure, monitor, and/or analyze ECOG signals. Additionally or alternatively, an external detection system or device such as an electroencephalography (EEG) system (e.g., a high density EEG system having 128, 256, or another number of channels) can detect neuroelectric signals. In such embodiments, particular electrophysiologic signal information can be measured or calculated. Electrophysiologic signal information can include one or more of power spectrum information (e.g., characteristics of, changes in, and/or relationships between particular spectral bands), coherence, and/or other information. For instance, spectral band power ratios corresponding to standard neuroelectric signal frequency ranges can be measured at one or more electrodes or electrode subsets. Such spectral power ratios can include one or more of an alpha/gamma ratio, an alpha/theta ratio, a theta/gamma ratio, and/or another ratio. In view of particular neural locations or areas corresponding to electrode subsets having an identical number of electrodes (e.g., 1 or 2 electrodes), a spectral power ratio associated with a first electrode subset that is significantly greater than or significantly less than (e.g., deviates by approximately 10%, 20%, or more from) an average spectral power ratio associated with other electrode subsets can indicate dysfunctional neural activity. Stimulation signals can be preferentially or exclusively applied to the patient using one or more electrodes or electrode subsets corresponding to a neural location at which a spectral power ratio significantly deviates from an average, expected, or desired spectral power ratio. The normalization or approximate equalization of spectral power ratios corresponding to one or more neural locations relative to an average spectral power ratio in surrounding or proximate neural locations can indicate a positive response to the neural stimulation signals. Stimulation parameters such as duty cycle, signal amplitude, signal polarity, pulse repetition frequency, and/or pulse width, can be adjusted or varied in order to enhance or maximize the degree to which the extrinsic neural stimulation normalizes or shifts particular power spectra ratios in a desired direction. In a manner analogous to that described above, different electrode subsets can be activated over time in the event that dysfunctional neuroelectric activity shifts to different neural locations.

As described in U.S. Patent Application Publication No. 20070265489, which is incorporated herein in its entirety by reference, the application of extrinsic stimulation signals can affect a patient's neurocognitive task performance (e.g., working memory and/or reaction time). An improvement in cognitive task performance during or after one or more therapy periods (one or more of which can span several weeks, months, or longer) can indicate that the extrinsic stimulation signals are facilitating a desired therapeutic effect.

In several embodiments, a threshold signal intensity or level corresponding to a given electrode subset can be determined by applying stimulation signals to this electrode subset, and measuring or estimating a minimum or near-minimum stimulation signal level that gives rise to a predetermined or minimum degree of change in neurocognitive task performance. A treatment signal intensity or level that is applied to the patient during a therapy period can be based upon a threshold signal level corresponding to one or more electrode subsets. For instance, a treatment signal level can be a given percentage of (e.g., approximately 20-95%, or approximately 50%, 80%, or 90% of) the activation threshold signal level corresponding to the particular electrode subset that gave rise to the lowest threshold signal level relative to each electrode subset considered. During a therapy period, a treatment signal can be applied to the particular electrode subset that gave rise to this lowest threshold level, and/or one or more other electrode subsets. In addition or as an alternative to the foregoing, a treatment signal intensity can be a mathematical function such as an average or a weighted average of a plurality of threshold signal intensities, where in some embodiments a weighting function can prioritize a threshold signal intensity associated with neurons in particular neural locations (e.g., more anterior neurons) more heavily than a threshold signal intensity associated with neurons within other (e.g., more posterior) neural locations.

In some patients experiencing readily or separately distinguishable neuropsychiatric and particular neurocognitive deficits or difficulties (both of which come within the scope of neurologic deficits), a first set or subset of electrodes directed toward treating neuropsychiatric dysfunction can be positioned both at and/or anterior to a distance $d_t$ within the middle frontal gyrus 1092 in a manner described above, and a second set or subset of electrodes directed toward treating neurocognitive dysfunction can be positioned posterior to $d_t$ within the middle frontal gyrus 1092. The first and second sets of electrodes can be carried by one or multiple support members. Between and/or within the first and second electrode subsets, the particular number of electrodes used to apply stimulation signals, and/or the amount of time that such electrodes are active, can depend upon the magnitude, extent, or degree of neuropsychiatric impairment relative to the magnitude or degree of neurocognitive impairment. As a representative example, for a patient experiencing a more significant degree of neuropsychiatric dysfunction than neurocognitive dysfunction, stimulation signals can be applied to a greater number of electrodes anterior to $d_t$ than posterior to $d_t$. Additionally or alternatively, stimulation signals can be applied at a higher signal level or more frequently (e.g., in accordance with a higher duty cycle) to those electrodes positioned anterior to $d_t$ than those electrodes that are positioned posterior to $d_t$. Analogous yet opposite considerations can apply to patients whose level of neurocognitive dysfunction substantially exceeds their level of neuropsychiatric dysfunction. Furthermore, the application of stimulation signals anterior and posterior to $d_t$ can be balanced or generally balanced in the event that a patient experiences substantially similar levels of impairment from both neuropsychiatric and neurocognitive dysfunction.

Additional Neuroanatomical Structure/Landmark/Reference Point Considerations

In addition or as an alternative to the foregoing, a target distance at or anterior to which stimulation signals can be preferentially applied to address neuropsychiatric dysfunction can be defined relative to a neuroanatomical structure other than the precentral sulcus 1091 or the central sulcus 1090. For example, the target distance can be determined relative to a predetermined location or boundary corresponding to the anterior extent of the lateral ventricles. This can include a location within the middle frontal gyrus 1092 that corresponds to a coronal brain section or plane that intersects the anterior extent of the lateral ventricles. In other embodiments, the target distance be distance away from a particular position upon the coronal suture that is expected or generally expected to correspond to a given anterior-posterior and superior-inferior location of or within the middle frontal gyrus 1092. As a representative example, Kido et al. indicate that the coronal suture can generally be expected to reside approximately 26 mm anterior to the intersection of the superior frontal sulcus and the precentral sulcus (see "Computed Tomographic Localization of the Precentral Gyrus," *Radiology* 135:373-377, May 1980, incorporated herein in its entirety by reference).

In various embodiments described above, the target distance $d_t$ is a target minimum distance away from a neuroanatomical reference point. In other embodiments, depending upon the particular neuroanatomical reference point that is selected, the target distance $d_t$ can be a target maximum distance away from the neuroanatomical reference point, at or anterior to which stimulation signals are preferentially applied or delivered to treat a neuropsychiatric disorder.

Figure 8:
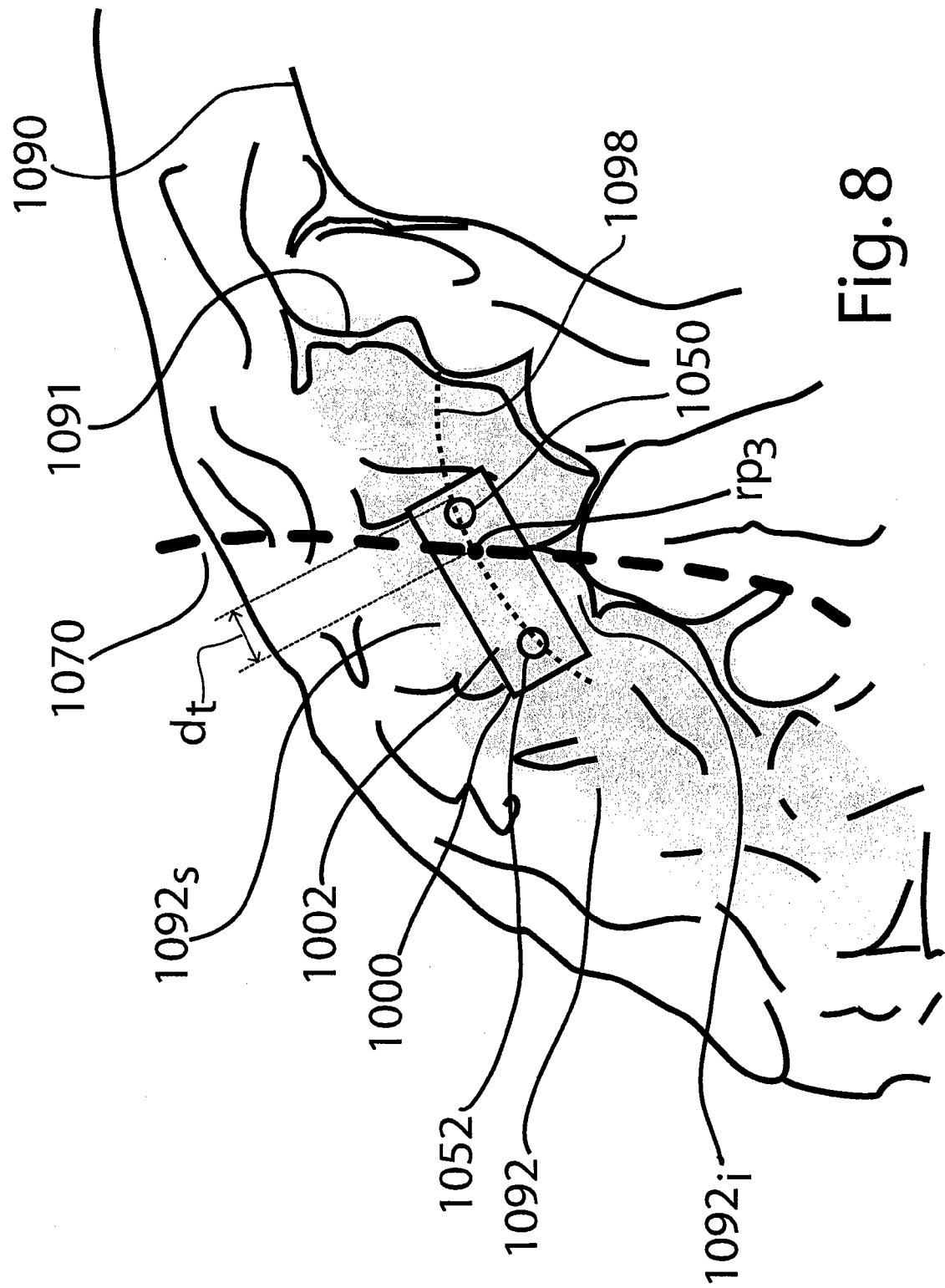
FIG. 8 is a schematic illustration of an electrode device implanted above or upon a patient's middle frontal gyrus in accordance with another embodiment of the disclosure.

FIG. 8 is a schematic illustration of an electrode device 1000 implanted above or upon a patient's middle frontal gyrus 1092 in accordance with another embodiment of the disclosure. In this embodiment, an anatomical reference point $rp_3$ can be defined as a point, location, or approximate location upon the coronal suture 1070 that corresponds or is expected to correspond to a particular middle frontal gyrus location. In general, the coronal suture 1070 can exhibit a certain thickness or width (e.g., 0.5-1.5 mm) depending upon patient anatomy. Accordingly, the target distance $d_t$ can be defined relative to an anterior edge or boundary of the coronal suture 1070, or a posterior boundary of the coronal suture 1070, or an approximate midpoint of the coronal suture's width. In at least some situations, defining $rp_3$ based upon an anterior coronal suture edge or border can increase the likelihood that stimulation signals are applied at and/or anterior to a middle frontal gyrus location that is appropriate for addressing a neuropsychiatric disorder.

In certain embodiments, an anatomical reference point $rp_3$ can be defined as a location or position on the coronal suture's anterior edge that resides, or which is expected to reside, directly above an approximate bisecting midline 1098 of the middle frontal gyrus 1092. A target distance $d_t$ can be defined to be approximately 2-12 mm posterior, or approximately 3-10 mm posterior, or approximately 4-7 mm posterior, or approximately 5 mm posterior to the coronal suture reference point $rp_3$. In one embodiment, the target distance $d_t$ is measured generally along and terminates directly or approximately directly above the middle frontal gyrus midline 1098. In a particular embodiment, an electrode device 1000 can be implanted such that the target distance $d_t$ spans the distance between the coronal suture reference point $rp_3$ and a posterior edge of a most posterior electrode 1050.

In various embodiments, stimulation signals can be applied (e.g., using a set of implanted electrodes) to neural populations that reside or approximately reside at or anterior to the target distance $d_t$. Thus, relative to the embodiment shown in FIG. 8, stimulation signals can be preferentially applied or directed to middle frontal gyrus neural populations that reside at or anterior to a target maximum posterior distance $d_t$ away from the coronal suture reference point $rp_3$.

As an alternative to the foregoing, in one embodiment, the target distance $d_t$ relative to the coronal suture reference point $rp_3$ can be approximately 0 mm. That is, a most posterior electrode 1050 of the electrode device 1000 can be implanted such that the electrode's posterior edge or center point resides or approximately resides directly beneath the coronal suture reference point $rp_3$.

Depending upon embodiment details, the electrode device 1000 can be implanted such that one or more electrodes 1050, 1052 reside along, generally along, or offset from the middle frontal gyrus midline 1098. In a manner analogous to that described above, based upon a coronal suture reference point $rp_3$ and a target distance $d_t$, an electrode device 1000 can be implanted such that an electrode 1050 resides at a superior offset distance $d_s$ (e.g., 1-5 mm) away from the middle frontal gyrus midline 1098. Stimulation signals can thus be applied to a superior portion of the middle frontal gyrus 1092, and/or a portion (e.g., an inferior aspect) of the superior frontal gyrus.

Additional Stimulation Site and Stimulation Technique Considerations

Figure 9:
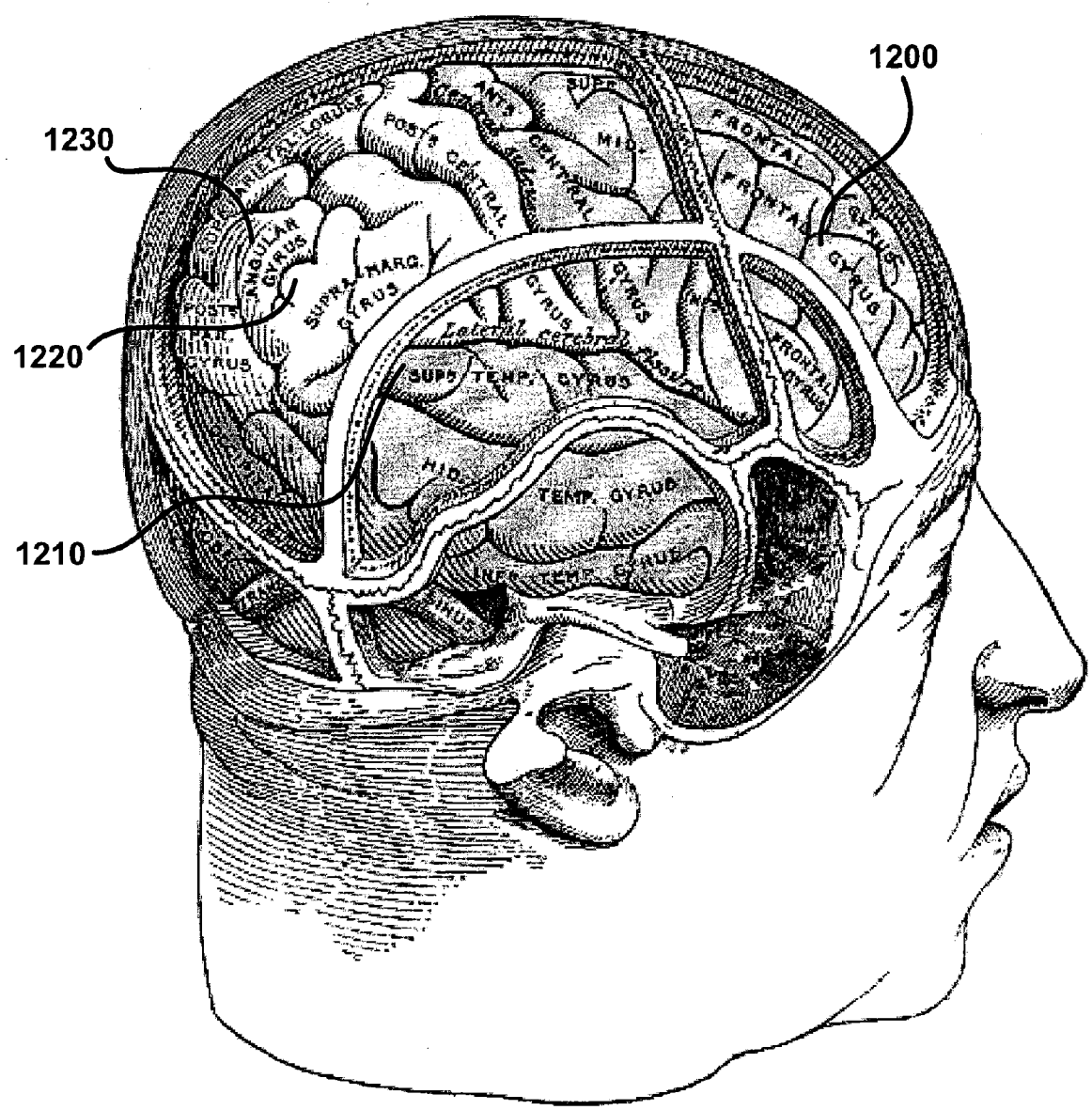
FIG. 9 is a cross-sectional illustration showing particular cortical areas of the human brain that reside beneath the dura and proximate to the skull.

FIG. 9 is a cross-sectional illustration showing particular cortical areas of the human brain that reside beneath the dura and proximate to the skull. The efficacy of extrinsic neural stimulation in treating certain neuropsychiatric disorders such as MDD, bipolar disorder, an anxiety-related disorder, schizophrenia, or another condition can be enhanced by applying stimulation signals to particular portions of the frontal or prefrontal cortex 1200 (e.g., Brodmann areas 9, 9/8, 46, 9/46, 8, 10, and/or 6) as well as one or more other cortical regions or areas that are known to be involved in the higher-order processing and interpretation of auditory information. Such cortical areas include portions of the posterior lateral superior temporal gyrus 1210, the supramarginal gyrus 1220, and the angular gyrus 1230. These cortical auditory processing areas 1210, 1220, 1230 have projections to and/or from non-superficial neural areas that are directly or indirectly involved in processing and interpreting the emotional content of incoming stimuli. The application of extrinsic stimulation signals to one or more of such higher-order auditory processing areas 1210, 1220, 1230 in one or both brain hemispheres can alter neural activity in a neural communication network that shares neurons or neural projections or communicates with another neural communication network involving portions of the prefrontal cortex 1200 e.g., the DLPFC, the OFC; and/or the Ventrolateral Prefrontal Cortex (VLPFC). Extrinsic stimulation signals can be applied to a higher-order auditory processing area using one or more types of signal delivery devices, such as those described herein.

Stimulation signals can be applied to particular portions of the prefrontal cortex 1200 in one or more manners previously described to treat neuropsychiatric dysfunction. Additionally or alternatively, neuropsychiatric dysfunction can be treated by applying stimulation signals to one or more of the aforementioned higher-order auditory processing areas 1210, 1220, 1230. In several embodiments, such stimulation signals can be applied to particular prefrontal and higher-order auditory areas in a simultaneous or serial/sequential manner. Additionally, neuroelectric signals can be measured using one or more electrodes implanted relative to one or more of such higher-order auditory processing areas 1210, 1220, 1230 in one or both brain hemispheres.

Similarities, differences, and/or correlations between neuroelectric signal information (e.g., spectral power band information or relationships) corresponding to one or more neural locations in the left brain hemisphere relative to homologous and/or non-homologous neural locations in the right brain hemisphere can indicate an extent to which neural stimulation is providing a desired effect. Such spectral power band information can be measured or generated in a manner that is identical or analogous to that described above. In the event that a particular stimulation regimen gives rise to a noticeable or measurable clinical response (e.g., as determined in association with a standardized assessment of neuropsychiatric function) as well as a measurable shift or change in one or more neuroelectric parameters (e.g., a shift toward a normalization or an approximate or average equalization of power spectra ratios between homologous and/or non-homologous neural areas), the detection of such shifts or changes in neuroelectric parameters can indicate whether particular stimulation parameters are likely to be effective before a clinical response that is determined in association with a standardized neuropsychiatric assessment can be reliably or repeatably determined. In the absence of such neuroelectric parameter shifts or changes during or after a therapy period (e.g., after several days or weeks), one or more stimulation signal parameters (e.g., signal intensity, pulse repetition frequency, signal polarity, and/or the particular electrode(s) or electrode subsets to which are active) can be changed in order to facilitate the initiation of such shifts.

From the foregoing, it will be appreciated that specific embodiments of the invention have been described herein for purposes of illustration, but that various modifications may be made without deviating from the invention. For example, at least some of the methods and systems described above may be used to treat neural populations other than those specifically described above. Aspects of the invention described in the context of particular embodiments may be combined or eliminated in other embodiments. Further, while advantages associated with certain embodiments of the invention have been described in the context of those embodiments, other embodiments may also exhibit such advantages, and not all embodiments need necessarily exhibit such advantages to fall within the scope of the disclosure. Accordingly, the invention can include embodiments not specifically shown or described above.

We claim:

1. A method for treating a patient's neurological disorder, comprising:

in a patient identified as having at least one of a neuropsychological disorder and a neuropsychiatric disorder, implanting at least one stimulation electrode within the patient's skull cavity, outside a cortical surface of the patient's brain, and at a location in a range of about 15 mm to about 35 mm anterior to a precentral sulcus reference point that is positioned (a) at the precentral sulcus and (b) at the patient's middle frontal gyrus; and treating the patient's disorder by applying electrical stimulation to the patient via the at least one stimulation electrode;

wherein:

the at least one stimulation electrode is one of a plurality of stimulation electrodes;

all of the active stimulation electrodes implanted within the patient's skull cavity are implanted outside the cortical surface of the patient's brain at the patient's middle frontal gyrus;

the at least one electrode is the posterior-most electrode within the patient's skull cavity and outside a cortical surface of the patient's brain via which electrical stimulation is applied to the patient's brain;

the at least one electrode is at least 18 mm anterior to the precentral sulcus reference point and is positioned superior to a linear or curvilinear line that at least bisects the middle frontal ayrus into a superior portion and an inferior portion; and the precentral sulcus reference point is approximately at an intersection of the precentral sulcus and the linear or curvilinear line.

2. The method of claim 1 wherein implanting at least one electrode includes implanting a plurality of electrodes, with at least one of the plurality of electrodes positioned more than 35 mm anterior to the precentral sulcus reference point.

3. The method of claim 1 wherein implanting the at least one electrode includes implanting a plurality of electrodes aligned generally parallel to a linear or curvilinear line that at least bisects the middle frontal gyrus into a superior portion and an inferior portion.

4. The method of claim 1 wherein implanting the at least one electrode includes implanting a plurality of electrodes, and wherein all of the stimulation electrodes implanted within the patient's skull cavity are implanted outside the cortical surface of the patient's brain at the patient's middle frontal gyrus.

5. The method of claim 1 wherein implanting the at least one electrode includes implanting a plurality of electrodes, and wherein all of the stimulation electrodes implanted within the patient's skull cavity are implanted outside the cortical surface of the patient's brain at least 15 mm anterior to the precentral sulcus reference point.

6. The method of claim 1 wherein all stimulation electrodes implanted within the patient's skull cavity are implanted outside the cortical surface of the patient's brain, and at a location in the range of about 15 mm to about 35 mm anterior to the precentral sulcus reference point.

7. The method of claim 1, further comprising directing the patient to engage in an adjunctive therapy as part of a treatment regimen that also includes the electrical stimulation.

8. The method of claim 7 wherein the adjunctive therapy includes at least one of a drug therapy, a behavioral therapy, a cognitive behavioral therapy, counseling, and biofeedback.

9. The method of claim 1 wherein implanting the electrode includes implanting the electrode at an epidural location.

10. The method of claim 1 wherein implanting the electrode includes implanting the electrode at a subdural location.

11. The method of claim 1 wherein the patient is diagnosed with a depressive disorder.

12. The method of claim 1 wherein the patient is diagnosed with a major depressive disorder.

13. The method of claim 1 wherein the patient is diagnosed with at least one of a mood disorder, bipolar disorder, obsessive-compulsive disorder (OCD), Tourette's syndrome, schizophrenia, a dissociative disorder, an anxiety disorder, a phobic disorder, a post-traumatic stress disorder, a borderline personality disorder, ADHD, and craving.

14. A method for treating a patient's neurological disorder, comprising:
   in a patient identified as having at least one of a neuropsychological disorder and a neuropsychiatric disorder, preferentially directing electrical stimulation to a target location of the patient's brain, the target location being in a range of about 15 mm to about 35 mm anterior to a precentral sulcus reference point that is positioned (a) at the precentral sulcus and (b) at the patient's middle frontal gyrus, with the electrical stimulation being directed from at least one stimulation electrode positioned within the patient's skull cavity and outside a cortical surface of the patient's brain;
   wherein:
      the at least one stimulation electrode is one of a plurality of stimulation electrodes;
      all of the stimulation electrodes within the patient's skull cavity are outside the cortical surface of the patient's brain at the patient's middle frontal gyrus;
      the at least one electrode is the posterior-most electrode within the patient's skull cavity and outside a cortical surface of the patient's brain via which electrical stimulation is applied to the patient's brain;
      the at least one electrode is at least 18 mm anterior to the precentral sulcus reference point and is positioned superior to a linear or curvilinear line that at least bisects the middle frontal gyrus into a superior portion and an inferior portion; and
      the precentral sulcus reference point is approximately at an intersection of the precentral sulcus and the linear or curvilinear line.

15. The method of claim 14, further comprising directing the patient to engage in an adjunctive therapy as part of a treatment regimen that also includes the electrical stimulation.

16. The method of claim 15 wherein the adjunctive therapy includes at least one of a drug therapy, a behavioral therapy, a cognitive behavioral therapy, counseling, and biofeedback.

17. The method of claim 14 wherein the patient is diagnosed with a depressive disorder.

18. The method of claim 14 wherein the patient is diagnosed with at least one of a mood disorder, bipolar disorder, obsessive-compulsive disorder (OCD), Tourette's syndrome, schizophrenia, a dissociative disorder, an anxiety disorder, a phobic disorder, a post-traumatic stress disorder, a borderline personality disorder, ADHD, and craving.

* * * * *